US009770529B2

(12) United States Patent
Downes et al.

(10) Patent No.: US 9,770,529 B2
(45) Date of Patent: Sep. 26, 2017

(54) TISSUE REPAIR SCAFFOLD

(75) Inventors: Sandra Downes, Manchester (GB); Lucy Ann Bosworth, Manchester (GB)

(73) Assignee: The University of Manchester, Manchester (GB)

( * ) Notice: Subject to any disclaimer, the term of this patent is extended or adjusted under 35 U.S.C. 154(b) by 271 days.

(21) Appl. No.: 13/158,550

(22) Filed: Jun. 13, 2011

(65) Prior Publication Data

US 2011/0238178 A1 Sep. 29, 2011

Related U.S. Application Data

(63) Continuation of application No. PCT/GB2009/002874, filed on Dec. 14, 2009.

(30) Foreign Application Priority Data

Dec. 12, 2008 (GB) .................................. 0822745.6

(51) Int. Cl.
*A61F 2/08* (2006.01)
*A61F 2/02* (2006.01)
*B29C 47/00* (2006.01)
*A61L 27/18* (2006.01)

(52) U.S. Cl.
CPC ..................... *A61L 27/18* (2013.01)

(58) Field of Classification Search
CPC ..................................................... B29C 47/00
USPC ......... 623/13.11–13.2; 606/228–231; 87/8, 9
See application file for complete search history.

(56) References Cited

U.S. PATENT DOCUMENTS

| 5,217,495 A | 6/1993 | Kaplan et al. |
| 6,045,571 A | 4/2000 | Hill et al. |
| 2003/0203003 A1 * | 10/2003 | Nelson et al. ................ 424/426 |
| 2005/0060033 A1 | 3/2005 | Vacanti et al. |
| 2006/0013869 A1 * | 1/2006 | Ignatious et al. ............. 424/464 |
| 2006/0154063 A1 * | 7/2006 | Fujihara et al. .............. 428/373 |

(Continued)

FOREIGN PATENT DOCUMENTS

| WO | WO 9614095 A1 * | 5/1996 |
| WO | WO 00/35507 | 6/2000 |

(Continued)

OTHER PUBLICATIONS

Cao et al., "Bridging Tendon Defects Using Autologous Tenocyte Engineered Tendon in a Hen Model", Tendon Tissue Engineering with Tenocytes, vol. 110, No. 5, 2001, pp. 1280-1289.

(Continued)

*Primary Examiner* — Yashita Sharma
(74) *Attorney, Agent, or Firm* — Seed IP Law Group LLP

(57) ABSTRACT

The present invention provides a tissue repair scaffold comprising a secondary fiber bundle, the secondary fiber bundle comprising a plurality of primary fiber bundles, each primary fiber bundle comprising a plurality of fibers, wherein the fibers comprise a biocompatible polymer. In embodiments the biocompatible polymer is polycaprolactone (PCL) (also known as poly-ε-caprolactone) and the average diameter of the fibers is less than 1 μm. The scaffold is particularly adapted for tendon repair. In vivo mouse studies demonstrate that tendon repair can be achieved with normal ambulation returning after 24-48 hours. The scaffolds were easy to handle during surgery, being non-slippery and easy to suture in place.

15 Claims, 20 Drawing Sheets

(56) References Cited

U.S. PATENT DOCUMENTS

| | | | |
|---|---|---|---|
| 2008/0028740 A1* | 2/2008 | Ushijima | D07B 1/025 57/204 |
| 2008/0188933 A1* | 8/2008 | Koob et al. | 623/13.12 |
| 2009/0287308 A1* | 11/2009 | Davis | A61F 2/08 623/13.12 |

FOREIGN PATENT DOCUMENTS

| WO | WO 01/32229 A1 | 5/2001 |
|---|---|---|
| WO | WO 2006/009315 A2 | 9/2006 |
| WO | WO 2006/106506 A2 | 10/2006 |
| WO | WO 2007/021590 A2 | 2/2007 |
| WO | WO 2007/024125 A1 | 3/2007 |
| WO | WO 2007/063820 A1 | 6/2007 |
| WO | WO 2007/071309 A2 | 6/2007 |

OTHER PUBLICATIONS

Cao et al., "In Vitro Tendon Engineering with Avian Tenocytes and Polyglycolic Acids: A Preliminary Report", Tissue Engineering, vol. 12, No. 5, 2006, pp. 1369-1378.
Casper et al., "Controlling Surface Morphology of Electrospun Polystyrene Fibers: Effect of Humidity and Molecular Weight in the Electrospinning Process", Macromolecules, 2004, 37, pp. 573-578.
Chew et al., "Aligned Protein-Polymer Composite Fibers Enhance Nerve Regeneration: A Potential Tissue-Engineering Platform", Adv. Funct. Mater, 2007, 17, pp. 1288-1296.
Crescenzi et al., "Thermodynamics of Fusion of Poly-B-Propiolactone and Poly-Caprolactone Comparative Analysis of the Melting of Aliphatic Polylactone and Polyester Chains", European Polymer Journal, 1972, vol. 8, pp. 449-463.
Curtis et al., "An In Vivo Microfabricated Scaffold for Tendon Repair", European Cells and Materials, vol. 9, 2005, pp. 50-57.
Deng et al., "Engineering human neo-tendon tissue in vitro with human dermal fibroblasts under static mechanical strain", Biomaterials, 30, 2009, pp. 6724-6730.
Dzenis, Yuris A., "Spinning Continuous Fibers for Nanotechnology", Science 304, Jun. 25, 2004, pp. 1917-1919.
Fong, et al., "Beaded nanofibers formed during electrospinning", Polymer 40, 1999, pp. 4585-4592.
Huang et al., "A review on polymer nanofibers by electrospinning and their applications in nanocomposites", Composites Science and Technology, 63, 2003, pp. 2223-2253.
Li et al., "Biological response of chondrocytes cultured in three-dimensional nonofibrous poly scaffolds", Wiley Periodicals, Inc., 2003, pp. 1105-1114.
Liu et al., "Repair of Tendon Defect with Dermal Fibroblast Engineered Tendon in a Porcine Model", Tissue Engineering, vol. 12, No. 4, 2006, pp. 775-789.
Maganaris et al., "In vivo human tendon mechanical properties", Journal of Physiology, 1999, 521.1, pp. 307-313.
Magnusson et al., "Differential strain patterns of the human gastrocnemius aponeurosis and free tendon, in vivo", Acta Physiol Scand, 2003, 177, pp. 185-195.
Mit-Uppatham et al., "Ultrafine Electrospun Polyamide-6 Fibers: Effect on Solution Conditions on Morphology and Average Fiber Diameter", Macromol. Chem. Phys., 2004, 205, pp. 2327-2338.
Reneker et al., "Bending instability of electrically charged liquid jets of polymer solutions in electrospinning", Journal of Applied Physics, vol. 87, No. 9, May 1, 2000, pp. 4531-4547.
Sato et al., "Reconstruction of rabbit Achilles tendon with three bioabsorbable materials: histological and biomechanical studies", J Orthop Sci, 2000, 5, pp. 256-267.
Shawon et al., "Electrospinning of polycarbonate nanofibers with solvent mixtures THF and DMF", Journal of Materials Science, 39, 2004, pp. 4605-4613.
Smit et al., "Continuous yarns from electrospun fibers", Polymer, 46, 2005, pp. 2419-2423.
Smith et al., "Evaluation of glutaraldehyde-treated tendon xenograft", The Journal of Hand Surgery, vol. 11A, No. 1, Jan. 1986, pp. 97-106.
Thomas et al., "Mechano-morphological studies of aligned nanofibrous scaffolds of polycaprolactone fabricated by electrospinning", J. Biomater. Sci. Polymer Edn, vol. 17, No. 9, 2006, pp. 969-984.
United Kingdom International Search Report, Application No. GB 0822745.6, Apr. 7, 2009.
Venugopal et al., "In vitro study of smooth muscle cells on polycaprolactone and collagen nanofibrous matrices", Cell Biology International, 29, 2005, pp. 861-867.
Wannatong et al., "Effects of solvents on electrospun polymeric fibers: preliminary study on polystyrene", Polymer International, 53, 2004, pp. 1851-1859.
Ramakrishna et al., "An Introduction to Electrospinning and Nanofibers", 2005 by World Scientific Publishing Co. Pte. Ltd., pp. 103-105.

* cited by examiner

TISSUE REPAIR SCAFFOLD

CROSS-REFERENCE TO RELATED APPLICATIONS

This application is a continuation of PCT/GB2009/002874, filed Dec. 14, 2009, which is hereby incorporated by reference in its entirety. PCT/GB2009/002874 claims the benefit of GB 0822745.6, filed Dec. 12, 2008, which is hereby incorporated by reference in its entirety.

FIELD OF THE INVENTION

The present invention is concerned with a tissue repair scaffold and a method of using the tissue repair scaffold, particularly in the treatment of damaged tendons.

BACKGROUND

Conventional approaches to the repair of tissue damage and assisting in the recovery from such damage are not comprehensive and have a number of drawbacks. Thus, tissue damage, and particularly damage to tendons, represents a significant challenge.

Tendons are a form of connective tissue and possess great flexibility and elasticity, which allow forces generated by muscle contraction to be transmitted to the attached bone, enabling movement. As a result of their ability to absorb external forces, tendons are able to act as a buffer, helping to prevent injury to the attached muscle.

Natural tendon is an example of a highly organised hierarchical tissue. It is principally composed of aligned collagen type I fibres with tenocytes arranged in rows between these fibres. Mechanical properties of tendons differ depending on their location within the body. In vivo studies on human Achilles' [Magnusson S P et al 2003] and tibialis anterior [Maganaris C N, 1999] tendons yielded moduli of 788 MPa and 1.2 GPa and tensile strengths 36.5 MPa and 25 MPa respectively. However, testing was not performed to rupture and can only be used as a guide.

All tendons have the potential to be affected by direct damage caused by lacerations or other accidental injuries. They are also susceptible to diseases. Clinically, tendon disorders are referred to as a "tendinopathy" as this makes no assumption as to the pathological processes within the tendon, although the term "tendonitis" is still used.

Of particular concern are tendinopathies within the Achilles tendon, which cause degeneration of the tissue. These are often the result of excessive and repetitive over-loading of the Achilles tendon in both sporting and sedentary patients.

Other tendons prone to pathology include the rotator cuff in the shoulder, where degeneration and the size of tears typically increases with age, and the patella tendon in the knee, which experiences degeneration due to excessive load bearing and strain rather than inflammatory tendinitis.

A variety of treatments are employed for tendinopathy management. In the early phase of disease, conservative methods (such as the use of non-steroidal anti-inflammatory drugs (NSAIDs) and corticosteroids) are customarily employed. For those patients who do not respond well to these treatments after 6 months, surgical intervention is common.

For patients presenting acute rupture of the Achilles tendon, treatment falls within three main categories—open operative, percutaneous operative and non-operative.

Open operative surgery involves the repair of the two ruptured ends of the tendon by suturing them together. Percutaneous operative is a combination of open and non-operative techniques and involves a number of small incisions used to suture the tendon without fully exposing the tissue. Non-operative treatments involve the immobilisation of the lower leg in a plaster cast for a period of 6-8 weeks.

Due to the often poor response to treatment, and resultant morbidity of tendon disease, there is a growing interest in novel techniques for repair of such tissues. Following injury, tendon heals by production of scar tissue, which is organisationally, biochemically and biomechanically inferior to normal tendon matrix tissue. Such inferior scar tissue leads to ongoing morbidity of affected patients.

Previous strategies employed to improve the quality of tendon repair after injury include xenograft tendons crosslinked with glutaraldehyde [Smith et al, 1986]. Tissue engineering approaches have utilised autologous tenocytes in biomaterial scaffolds [Cao et al, 2002]. Collagen-based scaffolds have been investigated in an attempt to match the mechanical properties with native tendon [Venugopal et al, 2005 and Curtis et al, 2005].

Synthetic bioresorbable polymers such as polycaprolactone (PCL), polylactic acid (PLA) and chitin have been formed as fibrous mats of randomly orientated fibres, but with limited success (Li et al, 2003).

SUMMARY OF THE INVENTION

The term "biocompatible polymer" as used herein will be familiar to the skilled reader but for completeness it pertains to a polymer which is compatible with natural tissue such that a significant immune response or other rejection response is not observed when the polymer is inserted (e.g. surgically implanted) into the human or animal body. The skilled reader will be aware of examples of biocompatible polymers, for example polycaprolactone, The terms "biodegradable polymer" and "bioresorbable polymer" as used herein will be familiar to the skilled reader but for completeness pertain to a polymer that breaks down and disperses in vivo.

The term "tissue repair" as used herein will be familiar to the skilled reader but for completeness it pertains to the repair of the natural tissue of a human or animal, for example by replacement or growth (including "regrowth") of that tissue.

The present invention seeks to address the drawbacks discussed above.

The present inventors have found that tissue repair and in particular tendon repair can be achieved by providing a tissue repair scaffold having a morphology and/or composition adapted to promote adhesion and growth of tendon cells, thereby facilitating tendon growth.

At its most general, the present invention proposes that a scaffold comprising fibres of a biocompatible polymer formed into bundles, which bundles are themselves formed into a secondary structure of fibre bundles, provides an effective mimic of natural tissue and in particular tendons. Another general proposition of the present invention is that a scaffold made from bundles of aligned fibres and/or twisted fibre bundles wherein the fibres comprise polycaprolactone is suitable for use in the repair of natural tissue and in particular tendons. These scaffolds are considered by the present inventors to provide a matrix that suitably not only exhibits appropriate biomechanical properties (particularly for tendon repair) but also facilitates growth of cells along and within the matrix. In a first aspect, the present invention provides a tissue repair scaffold comprising a secondary fibre bundle, the secondary fibre bundle comprising a plurality of primary fibre bundles, each primary fibre bundle comprising a plurality of fibres, wherein the fibres comprise a biocompatible polymer.

The discussion herein of the advantages associated with embodiments of the present invention is focused on tendon repair, but the scaffold and methods of the present invention are applicable more widely in tissue repair.

The present inventors have found that embodiments comprising this arrangement of fibres provide excellent biomechanical properties and an environment that promotes growth of tendons, in particular tendon cells such as tenocytes and chondrocytes.

The present inventors have found, through experimentation, that a scaffold comprising a secondary bundle structure formed from fibre bundles can encourage growth of tissue cells such as tenocytes. Without wishing to be bound by theory, the present inventors believe that the spaces (e.g. channels) between the primary fibre bundles facilitate tissue cell growth and mimic the spaces found within natural tendon units. In particular, in the case of tendon repair, the present inventors have found that the structure facilitates tendon cell growth along and within the scaffold.

Preferably the plurality of fibres are aligned. In other words, it is preferred that the fibres making up the primary bundle(s) are aligned, i.e. do not have a random orientation. Suitably at least 50% of the fibres that make up the primary bundle are aligned. More preferably at least 75% of the fibres that make up the primary bundle are aligned, and most preferably at least 90% are aligned.

Suitably the plurality of fibres (for example, at least 50% of the fibres that make up the primary bundle) are aligned such that their longitudinal axes lie within 30°, preferably within 20°, more preferably within 10° and most preferably within 5°, of each other.

Suitably the plurality of fibres (for example at least 50% of the fibres that make up the primary bundle) are substantially parallel. Suitably at least 50% of the fibres that make up the primary bundle are substantially parallel. More preferably at least 75% of the fibres that make up the primary bundle are substantially parallel, and most preferably at least 90% are substantially parallel.

Suitably the primary fibre bundle, suitably the secondary fibre bundle, and suitably the scaffold consists essentially of and preferably consists of the plurality of fibres.

Suitably the tissue is extracellular matrix (ECM). Preferably the tissue is a tendon. Examples of tendons for which the scaffold of the present invention is particularly effective include: Achilles tendon, Bicepes Brachii, Extensor Digitorum tendons, Extensor Indicis, Extensor Pollicis Longus, Supraspinatus tendon, Tibialis posterior tendons, Patella tendon and Peroneal tendons.

Suitably, the fibres consist essentially of and preferably consist of a biocompatible polymer. Thus, suitably the primary fibre bundles, suitably the secondary fibre bundle(s) and suitably the scaffold consists essentially of, preferably consists of, a biocompatible polymer. Thus, suitably the primary fibre bundles, suitably the secondary fibre bundle(s) and suitably the scaffold consist essentially of and preferably consist of biocompatible polymer fibres.

Whilst the scaffold of the first aspect may provide an effective scaffold for tissue repair with a wide range of biocompatible polymers, especially synthetic polymers, it is preferred that the biocompatible polymer is polycaprolactone (PCL) (also known as poly-ε-caprolactone). The biocompatible polymer, for example PCL, may be present as a homopolymer or a copolymer. The biocompatible polymer, for example PCL, may be present as part of a blend.

Alternatively or additionally, the biocompatible polymer may comprise one or more of (e.g. as a blend or copolymer) poly(lactic acid) PLA [in any one or more of its isomer forms: PLLA, PDLA and PDLLA], poly(glycolic acid) (PGA), poly(lactide-co-glycolide) (PLGA) [wherein the lactide component can be any one or more of the PLA isomers PLLA, PDLA and PDLLA] or poly(hydroxybutyrate) (PHB).

Nevertheless, it is preferred that the biocompatible polymers consists essentially of and preferably consists of PCL. Preferably the PCL is a homopolymer. Thus, suitably the primary fibre bundles, suitably the secondary fibre bundle(s) and suitably the scaffold consists essentially of, preferably consists of, PCL. Thus, suitably the primary fibre bundles, suitably the secondary fibre bundle(s) and suitably the scaffold consist essentially of and preferably consist of PCL fibres.

Preferably the polymer, suitably PCL, has a MW (Mn) of at least 10,000, more preferably at least 30,000 and most preferably at least 60,000. Preferably the MW (Mn) is no more than 200,000, more preferably no more than about 100,000. A particularly preferred MW (Mn) range is 60,000 to 100,000. A MW (Mn) of about 80,000 is especially preferred.

The present inventors have found that, particularly for tendon repair, it is advantageous for the primary fibre bundle(s) to be twisted. In embodiments, the provision of a twist facilitates the growth of tendon cells, especially tenocytes, along the fibre bundle. Preferred amounts of twist with reference to a helix angle are discussed herein with respect to the eleventh aspect, which also applies to this and other aspects. Additionally or alternatively, it is preferred that the amount or extent of twisting is selected so as to provide at least 100 turns per metre, more preferably at least 250 turns per metre, more preferably at least 400 turns per metre, more preferably at least 700 turns per metre, more preferably at least 900 turns per metre and most preferably at least 1000 turns per metre. Surprisingly, embodiments having such an extent of twist provide improved mechanical properties, for example with reference to one or more of modulus, tensile strength and strain. Embodiments demonstrate good elongation performance whilst benefiting from improved mechanical properties (for example, they may have improved tensile strength, but they remain capable of significant extension, thereby mimicking natural tendon tissue).

Twists can be in either the "S" or "Z" directions.

Suitably, in use, the fibre bundles are aligned with respect to the tissue that is being repaired. In particular, in the case of tendon repair, it is preferred that the longitudinal axis of the bundle is aligned with the longitudinal axis of the tendon that it is desired to repair.

Typically, the fibre bundles, and/or suitably the scaffold, has a length of up to 40 cm. In practice, an appropriate length is selected based on the tendon that is to be repaired.

The fibre bundles, and/or suitably the scaffold, may have a width from 50 μm to 10 cm or more. Again, in practice, an appropriate width is selected based on the tendon that is to be repaired.

Suitably the plurality of primary fibre bundles are arranged in a repeating structure. Preferably the plurality of primary fibre bundles are formed as a regular or ordered network or array. The present inventors have found that a regular repeating structure may assist in promoting cell growth along and within the scaffold. Such a structure may also provide desirable biomechanical properties. Indeed, suitably the primary fibre bundles are be arranged in any way that is appropriate to mimic the structure of natural tendons. In this connection, natural tendons come in many shapes and sizes, which reflects the numerous places in the body that they are found and the types and function of muscle to which they are connected. For example, natural tendons may have a morphology selected from cord or rope (e.g. with a substantially round cross-section), ribbon (e.g. flattened), band (e.g. strap-like) and fan. The scaffold of the present invention may have any one of these morphologies. Thus, suitably, the tissue repair scaffold has a morphology selected from: cord or rope, ribbon, band and fan.

Furthermore, the primary fibre bundles of the scaffold may be processed in the same way as any synthetic yarn or thread and may be woven, knitted, etc, to form a desired repeating structure. Indeed, in embodiments, the scaffold can comprise a yarn.

Thus, suitably the plurality of primary fibre bundles are intertwined. Preferably the primary fibre bundles are interlocked, suitably so as to impart strength and/or cohesion to the secondary fibre bundle(s).

Preferably the plurality of primary fibre bundles are plaited or twisted. Plaiting and twisting are preferred ways of achieving intertwining of the primary fibre bundles. Plaiting is particularly preferred because the channels or spaces are formed by virtue of the spaces between the plaited primary fibre bundles. This "porous" structure may assist the penetration of tissue cells into the scaffold.

Preferably the secondary fibre bundles have a rope-like morphology (for example, achieved by plaiting primary fibre bundles).

In embodiments, the secondary fibre bundles may be processed in the same way as natural or synthetic fibres (e.g. woven, knitted, etc), to control the overall morphology of the scaffold.

The present inventors have found that the average diameter of the fibres of the primary fibre bundles can be used to control not only the biomechanical properties of the scaffold but preferably also the effectiveness of the scaffold as an environment for encouraging cell growth. Preferably the average diameter of the fibres is less than 1.2 µm, more preferably less than 1 µm and most preferably less than 0.7 µm. The present inventors have found that fibre diameters in the nano scale (i.e. <1 µm) are particularly effective.

An advantage of the present invention is that the properties of the scaffold, including the biomechanical properties and suitably the effectiveness of the scaffold in encouraging cell growth, can be controlled by adjusting the average diameter of the primary fibre bundles. Preferably the average diameter of the primary fibre bundles is in the range 10-200 µm, more preferably in the range 30-100 µm. Suitably the average diameter of the secondary bundles is in the range 100-500 µm and most preferably in the range 150-400 µm.

Suitably the tissue repair scaffold comprises a plurality of secondary fibre bundles (for example, to form a tertiary fibre bundle structure). Alternatively, the scaffold may comprise only one secondary fibre bundle, for example to suit the tendon that is to be repaired.

The present inventors have found that electrospinning provides a particularly effective way of producing the tissue repair scaffold of the first aspect. Accordingly, it is preferred that the fibres are made by electrospinning.

Suitably the secondary bundle comprises at least 3 primary fibre bundles, preferably at least 5 primary fibre bundles.

In preferred embodiments, the primary fibre bundle comprises at least 50 fibres, more preferably at least 100 fibres.

The present inventors have found that such primary fibre bundles may provide a particularly effective mimic of tendon structure.

Suitably the tissue repair scaffold comprises collagen gel. The collagen gel suitably improves the growth of tendon cells (especially tenocytes) along and/or within the scaffold as compared to the scaffold without collagen gel.

In a second aspect, the present invention provides a tissue repair scaffold according to the first aspect for use in a method of treatment of the human or animal body. Suitably the method is a method of treatment by surgery.

Suitably the method comprises treating a damaged tendon.

Preferably the method comprises the step of attaching the tissue repair scaffold to a damaged tendon. Typically, this might be achieved by suturing the tissue repair scaffold to a damaged tendon.

In the case of treatment of animals, the animal is preferably a horse (e.g. a racehorse). Domestic pets such as one or more of dogs, cats and horses are preferred subjects for treatment. Animals in captivity, for example zoo animals, are also preferred subjects for treatment.

In a third aspect, the present invention provides a biocompatible polymer for use in a method of treatment of a damaged tendon, wherein the biocompatible polymer is in the form of a tissue repair scaffold according to the first aspect.

In a related aspect, the present invention provides a use of a biocompatible polymer in a method of manufacturing a tissue repair scaffold according to the first aspect for treatment of a damaged tendon.

In a fourth aspect, the present invention provides a method of treating a damaged tissue, the method comprising the step of attaching a tissue repair scaffold according to the first aspect to the damaged tissue. Suitably the tissue is a tendon.

Suitably the step of attaching comprises grafting the tissue repair scaffold to the damaged tendon.

In a fifth aspect, the present invention provides a method of making a tissue repair scaffold, the method comprising the steps of
(A) electrospinning a plurality of fibres, the fibres comprising a biocompatible polymer;
(B) forming a primary fibre bundle from the plurality of fibres; and
(C) forming a secondary fibre bundle from a plurality of primary fibre bundles.

Suitably the tissue repair scaffold is a tissue repair scaffold according to the first aspect.

In a sixth aspect, the present invention provides a tissue repair scaffold comprising a fibre bundle, the fibre bundle comprising a plurality of aligned fibres, wherein the fibres comprise polycaprolactone (PCL).

Preferably the tissue is a tendon. Suitably the fibres are as defined in the first aspect. Suitably the fibre bundle has the features of the primary fibre bundle as defined in the first aspect. Optionally, the features of the scaffold of the first aspect also apply to this aspect.

In particular, suitably the scaffold comprises a plurality of fibre bundles arranged in a repeating structure. Preferably the plurality of fibre bundles are formed as a regular or ordered network or array. Suitably the plurality of fibre bundles are formed into secondary bundles. Furthermore, the fibre bundles of the scaffold may be processed in the same way as any synthetic yarn or thread and may be woven, knitted, etc, to form a desired repeating structure. Indeed, in embodiments, the scaffold can comprise a yarn.

In a seventh aspect, the present invention provides a tissue repair scaffold according to the sixth aspect for use in a method of treatment of the human or animal body. Suitably the method is a method of treatment by surgery.

Preferably the method comprises treating a damaged tendon.

Preferably the method comprises the step of attaching, preferably grafting, the tissue repair scaffold to a damaged tendon. Typically, this might be achieved by suturing the tissue repair scaffold to a damaged tendon.

In the case of treatment of animals, the animal is preferably a horse (e.g. a racehorse), cat or dog. Preferably the animal is an animal in captivity, such as a zoo animal.

In an eighth aspect, the present invention provides polycaprolactone (PCL) for use in a method of treatment of a damaged tendon, wherein the PCL is present in a tissue repair scaffold according to the sixth aspect.

In a related aspect, the present invention provides a use of polycaprolactone (PCL) in a method of manufacturing a tissue repair scaffold according to the sixth aspect for treatment of a damaged tendon.

In a ninth aspect, the present invention provides a method of treating a damaged tissue, the method comprising the step of attaching a tissue repair scaffold according to the sixth aspect to the damaged tissue. Suitably the tissue is a tendon.

Suitably the step of attaching comprises grafting the tissue repair scaffold to the damaged tendon.

In a tenth aspect, the present invention provides a method of making a tissue repair scaffold, the method comprising the steps of
(A) electrospinning a plurality of aligned fibres, the fibres comprising polycaprolactone; and
(B) forming a fibre bundle from the plurality of aligned fibres.

Suitably the tissue repair scaffold is a tissue repair scaffold according to the sixth aspect.

In an eleventh aspect, the present invention provides a tissue repair scaffold comprising a twisted fibre bundle, wherein the twisted fibre bundle comprises a plurality of fibres, the fibres comprising polycaprolactone.

Suitably the twisted fibre bundle is such that the fibres form a helix. Preferably the helix angle (the angle formed between the direction of the fibres and the longitudinal axis of the fibre bundle) is in the range 10° to 80°, more preferably 20° to 80°, and most preferably 20° to 60°. As discussed above, the helix, and the preferred helix angle, also applies to the fibre bundles of the other aspects.

Preferably the tissue is a tendon.

Suitably the fibres are as defined in the first aspect. Preferably the twisted fibre bundle has the features of the primary fibre bundle as defined in the first aspect. Optionally, the features of the scaffold of the first aspect also apply to this aspect.

In particular, suitably the scaffold comprises a plurality of fibre bundles arranged in a repeating structure. Preferably the plurality of fibre bundles are formed as a regular or ordered network or array. Suitably the plurality of fibre bundles are formed into secondary bundles. Furthermore, the fibre bundles of the scaffold may be processed in the same way as any synthetic yarn or thread and may be woven, knitted, etc, to form a desired repeating structure. Indeed, in embodiments, the scaffold can comprise a yarn.

In a twelfth aspect, the present invention provides a tissue repair scaffold according to the eleventh aspect for use in a method of treatment of the human or animal body. Suitably treatment is by surgery.

Preferably the method comprises treating a damaged tendon.

In the case of treatment of animals, the animal is preferably a horse (e.g. a racehorse), cat or dog. Preferably the animal is an animal in captivity, such as a zoo animal.

In a thirteenth aspect, the present invention provides polycaprolactone (PCL) for use in a method of treating a damaged tendon, wherein the PCL is present in a tissue repair scaffold according to the eleventh aspect.

In a related aspect, the present invention provides a use of polycaprolactone (PCL) in a method of manufacturing a tissue repair scaffold according to the eleventh aspect for treatment of a damaged tendon.

In a fourteenth aspect, the present invention provides a method of treating a damaged tissue, the method comprising the steps of attaching a tissue repair scaffold according to the eleventh aspect to the damaged tissue. Suitably the tissue is a tendon.

Suitably the step of attaching comprises grafting the tissue repair scaffold to the damaged tendon.

In a fifteenth aspect, the present invention provides a method of making a tissue repair scaffold, the method comprising the steps of:
(A) electrospinning a plurality of fibres, the fibres comprising polycaprolactone;
(B) forming a fibre bundle from the plurality of fibres; and
(C) twisting the fibre bundle.

Preferably the tissue repair scaffold is a tissue repair scaffold according to the eleventh aspect.

In a sixteenth aspect the present invention provides a synthetic tendon, wherein the synthetic tendon is as defined in any one of the first, sixth and eleventh aspects.

In embodiments, the tissue repair scaffold of any of the aspects is provided in a sterile enclosure, for example a sterile packet. Suitably the enclosure is hermetically sealed.

Thus, in a seventeenth aspect the present invention provides a tissue repair scaffold according to any one of the aspects herein, wherein the tissue repair scaffold is provided in a sterile enclosure.

It is envisaged that the tissue repair scaffold may be provided in a variety of different sizes and morphologies, for example in a number of "off the shelf" configurations, so as to enable a surgeon to select the most appropriate scaffold for the tissue that is to be repaired. Thus, in an eighteenth aspect, the present invention provides a kit comprising a plurality of tissue repair scaffolds, each scaffold being a scaffold according to any one of the aspects herein, wherein each scaffold is provided in a sterile enclosure. Suitably at least some of the scaffolds are different, e.g. have different dimensions and/or morphologies.

In an eighteenth aspect, the present invention provides a tissue repair scaffold made according to a method as described in any one of the other aspects. Suitably the method is a method of any one of the fifth, tenth or fifteenth aspects.

Any one of the aspects of the present invention may be combined with any one or more of the other aspects. Furthermore, any of the optional or preferred features of any one of the aspects may apply to any of the other aspects. In particular, optional features associated with a method or use may apply to a scaffold, and vice versa.

BRIEF DESCRIPTION OF THE DRAWINGS

Embodiments of the invention and experiments illustrating the advantages and/or implementation of the invention are described below, by way of example only, with respect to the accompanying drawings, in which.

DETAILED DESCRIPTION OF CERTAIN EMBODIMENTS AND EXPERIMENTS

Figure 1:
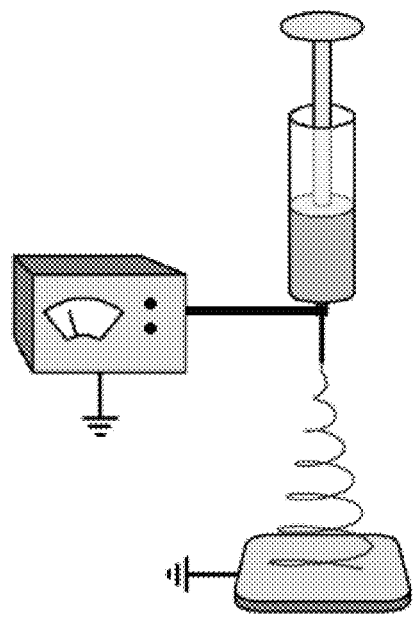
FIG. 1 shows a schematic of the electrospinning apparatus used to make the fibres for inclusion in scaffolds of the present invention.

A number of examples of three-dimensional electrospun bundles of aligned fibres made from PCL are described herein. These fibrous constructs are intended to mimic both the morphological anatomy and the biomechanical properties of natural human tendon. This tissue is known to be composed of a hierarchical organisation of aligned collagen fibres, and these bundles are representative of certain parts of the overall tendon. In embodiments, whilst the fibres contained within the PCL bundles are not of the same size as the collagen fibres, the gross morphology of the fabricated 3D bundles closely resembles those within the natural tendon tissue.

The fibre bundles described herein are biodegradable and/or bioresorbable. This suitably eliminates the need for secondary surgery. Furthermore, in embodiments, the rate of degradation matches the rate of new tissue formation. Preliminary studies suggest that the degradation rates are suitable for accommodating natural healing times for tendons of about three months.

Testing of embodiments has shown that the fibre bundles (scaffolds) are able to withstand high tensile loads and demonstrate flexibility. This latter characteristic is particularly promising given that some tendons are required to bend round bony prominences.

Described herein are studies which demonstrate how electrospinning of fibres can be used to produce the scaffolds of the present invention. Furthermore, the results of studies by the present inventors show how variation of the parameters associated with electrospinning can be used to control the fibre characteristics.

Furthermore, the mechanical properties of bundles derived from four electrospinning methods were compared. Fibre bundles were either drawn from the surface of a liquid reservoir or fibres were twisted into three-dimensional (3D) constructs following spinning between fixed plates or on thin edged or fine edged rotating mandrels.

(1) Fibre Formation (a) Electrospinning and Selection of Parameters

Electrospinning provides a way of generating fibres of controlled diameter. In particular, electrospinning enables the fabrication of long, continuous fibres of controlled diameter. At its simplest, the application of a high voltage to a polymer solution within a syringe causes expulsion of a polymer jet towards an earthed collector.

It is possible to electrospin a wide range of polymers, including biocompatible polymers.

A number of parameters can be used to control the properties of the fibres formed using electrospinning. The following parameters are mentioned as particularly useful in controlling the collected fibres:

1. Solvent
2. Molecular weight of polymer
3. Concentration of polymer-solvent solution
4. Applied voltage
5. Tip to collector distance
6. Flow rate of polymer-solvent solution These and other parameters are discussed in more detail below.

Solvent

Suitable solvents include acetone, chloroform, dichloromethane (DCM) and tetrahydrofuran (THF). Hexafluoroisopropanol (HFIP) can also be used.

Experiments were conducted in order to demonstrate the affect of solvent selection on fibre formation. PCL (Mn 80,000) (Sigma Aldrich) was dissolved in four separate solvents to give concentrations of 10% w/v. The four solvents were; acetone, chloroform, dichloromethane (DCM) and tetrahydrofuran (THF). Each polymer-solvent was electrospun with flow-rate 0.1 ml/min, voltage 15 kV and needle-tip to collector distance 5 cm.

Conclusion: Investigations for determining the ideal solvent for electrospinning PCL resulted in solvent with highest dielectric constant yielding the greatest number of fibres due to the charge repulsion interactions which occur as the polymer jet travels towards the collector. The preferred solvent from this study was acetone and this was used for all subsequent electrospinning of PCL.

Molecular Weight of Polymer

A suitable molecular weight (Mn) is in the range 10,000 to 100,000, but other molecular weights can be used, as described herein.

Experiments were conducted in order to demonstrate the affect of polymer molecular weight on fibre formation. Two batches of PCL with number average molecular weight (Mn) of 40,000 and 80,000 were separately dissolved in acetone at concentrations of 10% w/v. These two batches were electrospun separately under the same conditions: flow-rate 0.05 ml/min, voltage 25 kV and needle-tip to collector distance 10 cm.

Conclusion: SEM analysis showed that molecular weight had a significant affect on the fibre morphology. The PCL of higher molecular weight (Mn 80,000) was found to minimise the occurrence of "beads" along the fibres.

Concentration of Polymer-Solvent Solution

Suitable concentrations are in the range 3% w/v to 15% w/v, preferably 5% w/v to 10% w/v.

Experiments were conducted in order to demonstrate the affect of polymer-solvent solution concentration on fibre formation. Solution concentrations investigated were 5% w/v, 7.5% w/v and 10% w/v. Polymeric solutions were prepared by weighing out a known quantity of PCL (Mn 80,000) into a glass jar together with a known volume of acetone. The same solvent was used throughout the study. The glass jar was sealed and placed on a stirrer (Stuart SB162) until the polymer dissolved.

Conclusion: The fibre diameter can be tailored by altering the solution concentration. Generally, it was found that higher concentrations resulted in fibres of greater diameter.

Voltage

The voltage applied to the polymeric solution has a direct affect on fibre morphology. High voltage causes the polymer jet to be emitted with rapid acceleration, limiting the jets flight time and subsequently decreases the amount of stretching and solvent evaporation prior to collector impact [Ramakrishna et al, 2005]. The resulting fibres may be thicker and contain high levels of residual solvent. The flight time of the polymer jet is, however, dependent upon the tip to collector distance.

Experiments were conducted in order to demonstrate the affect of voltage on fibre formation. The electrospinning process was performed using two separate voltages: 25 kV and 15 kV. The voltage was set to the desired value prior to the start of electrospinning, thus ensuring all fibres collected were subjected to the same voltage. Voltage was supplied by FC Series 120 Watt regulated high voltage DC power supply from Glassman High Voltage, Inc.

Conclusion: It was found that keeping the applied voltage comparatively low (e.g. 15 kV) was effective in producing electrospun fibres of fine, submicron diameter. Nevertheless, it was found to be desirable to avoid much lower voltages so as to ensure sufficient electro-static charging of the polymer solution and ejection of a polymer jet.

Needle-Tip to Collector Distance

Varying the distance between the needle-tip to the collector has an important role in determining fibre characteristics. A short deposition distance reduces the polymer jet flight time, limiting the rate of solvent evaporation and polymer stretching; often resulting in the fabrication of thick, merged fibres. Generally, a minimum distance, which allows significant drying and stretching of the jet, is required for the production of long, fine fibres [Reneker et al, 2000].

Experiments were conducted in order to demonstrate the affect of needle-tip to collector distance on fibre formation. Needle-tip to collector distances of 5 cm and 10 cm were tested. This was achieved by adjusting the height of the collector plate to the required distance before the electrospinning process was started.

Conclusion: The deposition distance between the needle-tip and collector should be long enough to ensure adequate time for the polymer jet to undergo sufficient stretching and solvent evaporation prior to its impact.

Flow Rate of Polymer-Solvent Solution

The applied flow rate determines the quantity of polymeric solution available to the electrospinning process. Generally, high flow rates yield fibres of larger diameter. This is because the greater volume of solution pumped out may not have sufficient time for solvent evaporation and adequate stretching of the jet prior to contact with the collector.

Experiments were conducted in order to demonstrate the affect of flow rate on fibre formation. A polymer-solvent solution was poured into a 50 ml syringe (BD Plastipak) and placed within a syringe pump (SP230lW2—World Precision Instruments). The flow rates applied during electrospinning were 0.1 ml/min and 0.05 ml/min.

Conclusion: It was found that it is desirable to use a low flow-rate and that high flow rates may result in fibres of wider diameter (e.g. larger than 1 μm).

Solution Viscosity

The viscosity of solution is directly affected by the concentration of polymer present. If the polymer concentration is high, greater quantities of polymer chains are present, increasing the number of chain entanglements with solvent molecules and ultimately raising solution viscosity. A polymer's molecular weight also affects solution viscosity. A polymer of low molecular weight reduces the number of solvent/polymer entanglements because of the shorter length chains, and hence decreases solution viscosity. Fibre production is dependent on the concentration of solution being electrospun.

Generally, if the concentration is too low bead formation as opposed to fibre production is observed; and if too high, pumping of the solution will be difficult and fabricated fibres are mostly micrometre in diameter.

Solution Conductivity

The solvent chosen to dissolve the polymer has a significant role in the level of conductivity present within the solution, and this directly affects the fibre morphology generated from the electrospinning process. Solvents with high dielectric constants cause the emitted polymer jet to experience increased longitudinal force brought about by the higher accumulation of charge present within the polymeric solution [Wannatong et al, 2004]. Consequently the polymer jet experiences a greater degree of charge repulsion, leading to an increased level of stretching and elongation, resulting in fibres of finer diameter [Fong et al, 1999].

Surface Tension

The surface tension of the polymeric solution must be overcome in order for the electrospinning process to be initiated. The polymeric solutions viscosity directly affects its surface tension; high viscosity reduces the surface tension due to significant entanglement between solvent molecules and polymer chains preventing molecule clustering [Shawon and Sung, 2004].

Humidity

The humidity surrounding the electrospinning process can have a significant affect on fibre morphology, in terms of surface porosity: rising levels of humidity lead to an increase in pore size, number and distribution over the fibre surface [Casper et al, 2004].

Temperature

Increasing the polymeric solution temperature may result in a faster rate of fibre deposition and fibres may therefore have a decreased diameter. These effects may be attributed to the reduced viscosity of polymeric solution caused by decreased entanglements between polymer and solvent molecules as a result of polymer chain expansion [Mit-uppatham et al, 2004].

(b) Fibre Orientation

Fibre Alignment and Collector Method

The orientation of fibres deposited from the electrospinning process is dependent upon their method of collection. Fibre alignment is determined by the angle between the fibre and the direction of alignment—the smaller the angle the greater the alignment.

Random, non-woven arrangements of fibres are created when the collector is an earthed stationary plate.

Purposefully orientated fibres can be fabricated by electrospinning between the gap of two fixed metal plates or onto a mandrel rotating at an optimised speed. Indeed, collection of fibres between two parallel earthed plates, also known as 'gap method of alignment' may be used to produce aligned fibres (Dzenis, 2004).

Fibrous yarns containing aligned individual fibres that are grouped together can also be fabricated by spinning the polymer solution directly into an earthed liquid reservoir (Smit et al, 2005). The network of fibres collected on the liquid surface is drawn off and into the air. Fibres align and coalesce due to the effects of surface tension between the fibres and liquid during the drawing process. Three-dimensional fibrous bundles are the end product after lifting the fibres off the liquid surface.

Another method for aligned fibre formation requires the use of a rotating mandrel. Generally, the mandrel must be rotated at sufficient speed so as to ensure that rotation speed is not too slow compared to the speed of fibre emission, in which case alignment may be inhibited. Similarly, if rotation is too fast fibre breakage can occur [Huang et al, 2003].

The various methods for fibre collection resulted in different fibre orientation. As might be expected, the stationary plate produced fibres with least alignment. Collection on the rotating mandrel resulted in fibres of greatest alignment.

Further experiments examined the selection of mandrel rotation speed as a function of mandrel dimensions.

Optimising Rotation Speed for Creating Aligned Fibres on a Mandrel

Experiments showed that the orientation of fibres when collected on a mandrel depends on the mandrel's rotation speed. For a narrow mandrel (width=3 mm; diameter=120 mm), low speeds of 300 RPM resulted in fibre deposition similar to the fibrous networks collected on stationary plates. If the speed of rotation was too fast, the fibres appeared to predominantly random in appearance. At an optimal speed the fibres were collected parallel to the direction of rotation. 500-600 RPM (e.g. 500 RPM) resulted in the greatest alignment.

A second mandrel, being wider (width=90 mm; diameter=65 mm) than the first mandrel, was tested and the optimum rotation speed for alignment of fibres was found to be different to that for the narrow mandrel. For the wide mandrel, speeds of 1200 RPM and greater were employed to generate sufficiently aligned fibres.

Measurement of the angle of these fibres with respect to the longitudinal axis showed that when rotated at a speed of 1800 RPM the lowest angle of alignment was achieved and hence greatest degree of parallelism to the longitudinal axis. The results would suggest alignment may be further increased at rotation speeds above 1800 RPM.

(c) Surface Characteristics

The wettability of the scaffold surface is a characteristic of the scaffold that can be adjusted to suit the function of the scaffold. Suitably, to encourage cell attachment, the exterior of the material is hydrophilic or wettable as this will permit cells to contact with the surface over a greater area to allow attachment and spreading, and for providing cells with an environment similar to their natural environment. To discourage cell attachment or protein adhesion, however, hydrophobic or non-wetting surfaces can be created. The skilled reader is familiar with appropriate surface treatments.

(2) Scaffold Formation

Unless otherwise stated, the electrospinning parameters employed for the fabrication of all electrospun fibre matrices were as follows: voltage 20 kV (Series 120 Watt regulated high voltage DC power supply, Glassman High Voltage, Inc) flow-rate 0.05 ml/min (SP230lW2, World Precision Instruments), needle-tip (Ø0.8 mm, BD Microlance) to collector distance 15 cm and solution concentration 10% w/v polycaprolactone (PCL) (80,000 Mn) (Sigma Aldrich) in Acetone. For 2D fibrous mats, electrospinning was conducted for a period of 30 minutes; 3D fibrous bundles, spinning time was reduced to 15 minutes.

Samples were tested within 48 hours of spinning, to minimise the risk of atmospheric effects and annealing of the PCL fibres. Samples were stored at 4° C. in a desiccator until required.

Fibre Bundle Formation

All needles had the tip removed and the edge smoothed before use. This was to allow for an evenly formed droplet at the end of the needle-tip.

Four different types of fibre bundle were produced. Liquid reservoir (LR) bundles were created by spinning directly onto the surface of distilled water contained within an earthed foil tin. Once a thin film of fibres had been deposited on the waters surface the electrospinning process was cut-off. Using the tip of a needle, fibres were drawn off from the liquid surface as three-dimensional bundles and left to dry.

Figure 2:
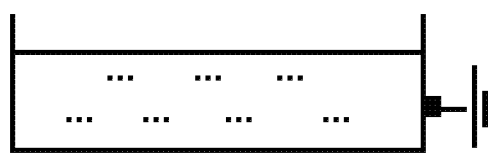
FIG. 2 shows a schematic of the liquid reservoir electrospinning apparatus used in an embodiment of the present invention.

This is shown schematically in FIG. 2. As the fibres are removed from the surface, the effect of surface tension from the liquid causes the fibres to align and coalesce, creating 3D fibrous bundles.

Figure 3:
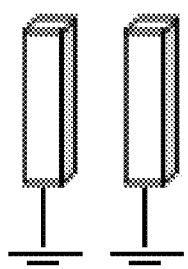
FIG. 3 shows a schematic of the fixed point electrospinning apparatus used in an embodiment of the present invention.

Fixed point (FP) bundles were made from fibres spun between two earthed stainless steel plates, placed 3 cm apart. This is shown schematically in FIG. 3. For each sample created, the electrospinning process was run for 90 seconds. After this time, the bridged fibres were carefully submerged in distilled water causing the separate fibres to group together. The plates were then rotated, twisting the grouped fibres to produce robust fibrous three-dimensional bundles. These were removed from the plates and left to dry. Purpose made mandrels of aluminium with diameter 120 mm and edge thickness of 3 mm (Fine Mandrel—FM) and 5 mm (Thin Mandrel—TM) respectively were mounted on a non-conductive Tufnol rod. Fibres were spun onto the edge of each mandrel rotating at a speed of 600 rpm for 2 minutes, as this was sufficient time for complete coverage of the mandrel edge. The mat of fibres deposited on the mandrel edge was removed as a single long strip and cut every 3 cm along its length into smaller sheets. Each sheet of fibres was then submerged in distilled water and twisted to form a three-dimensional bundle, which was then left to dry.

Figure 4:
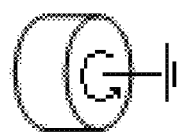
FIG. 4 shows a schematic of the fine mandrel electrospinning apparatus used in an embodiment of the present invention.
Figure 5:
FIG. 5 shows a schematic of the thin mandrel electrospinning apparatus used in an embodiment of the present invention.

Fibres were spun onto the edge of custom made, stainless steel, fine (3 mm) or thin (5mm) rotating mandrels as shown schematically in FIGS. 4 and 5. The processes employing the different mandrels are denoted FM and TM for fine mandrel and thin mandrel respectively. Fibres were spun onto the edge of each mandrel rotating at a speed of 600 rpm for 2 minutes, as this was sufficient time for complete coverage of the mandrel edge. The mat of fibres deposited on the mandrel edge was removed as a single long strip and cut every 3 cm along its length into smaller sheets. Each sheet of fibres was then submerged in distilled water and twisted to form a three-dimensional bundle, which was then left to dry.

Secondary Fibre Bundle Formation

A number of bundles created by the rotating mandrel edge method were used to produce two different rope-like configurations: plait and twist. In the first example, two sets of tweezers were used to plait three bundles together. In the second example, three bundles laid parallel to each other and manually twisted together.

(3) Characterisation of Scaffold

SEM—Fibres and Primary Bundles

The structural morphologies of the different fibrous bundles were assessed by SEM (Topcon SM-300) analysis using an accelerating voltage of 5 keV with a working distance of 8 mm. Samples were mounted onto separate carbon-coated stubs (Agar Scientific) and gold-sputter coated for a total of 2 minutes (Edwards Sputter Coater—S150B). During the first minute samples were laid flat pointing upwards; samples were then placed on their edge (lying approximately 45° to the vertical) and coated for 30 seconds; rotating 180° about this edge, samples were coated for the final 30 seconds. This ensured adequate coverage and prevented charging within the SEM chamber.

Image tool for Windows version 3.00 was used to measure the diameter of bundles from microscopy images. The diameters of 50 randomly selected fibres per concentration were measured.

To determine fibre alignment the collected fibres were viewed under the SEM and between 70 and 80 fibres were measured according to their alignment with the longitudinal axis (straight line from the top to the bottom of the micrograph) using Image tool for Windows version 3.00. The angle of the fibres was determined by selecting the "angle" icon and measuring the angle between the fibres to the longitudinal axis. Results were transferred to Microsoft Excel for further analysis.

Figure 6:
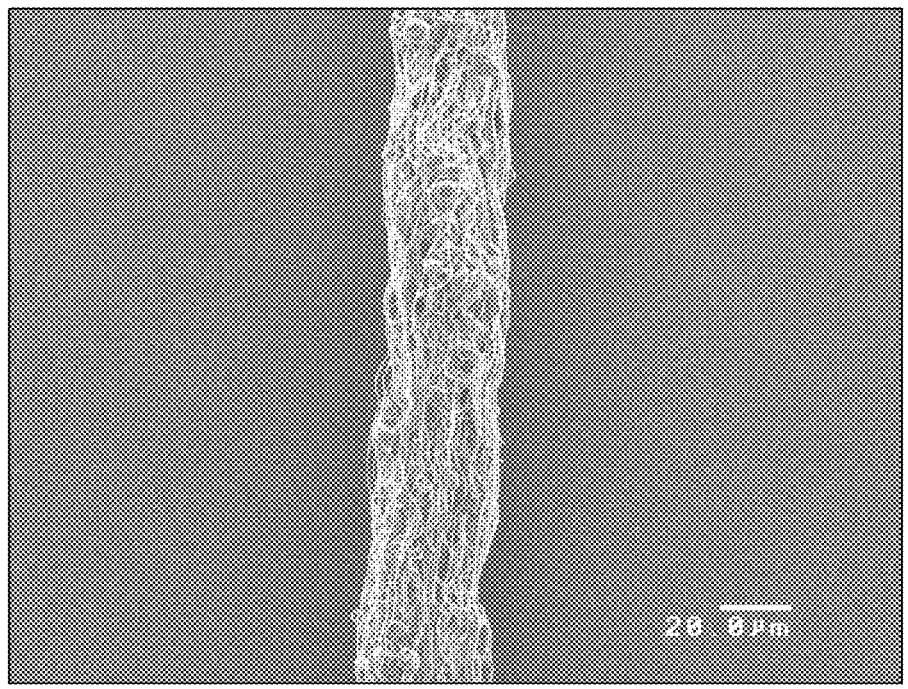
FIG. 6 shows an SEM micrograph of a fibre bundle formed using the liquid reservoir method.
Figure 7:
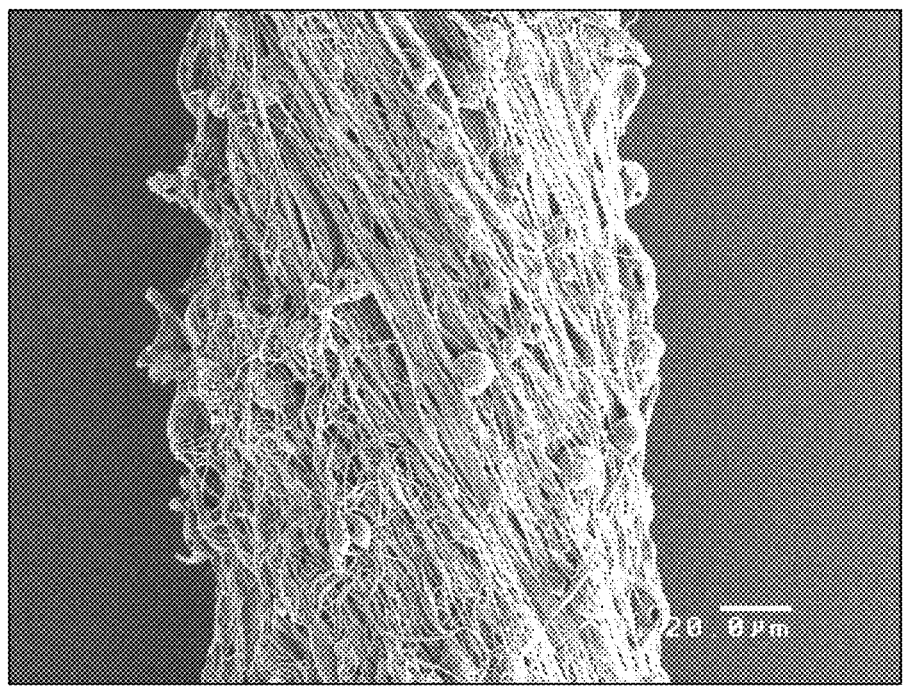
FIG. 7 shows an SEM micrograph of a fibre bundle formed using the fixed point method.
Figure 8:
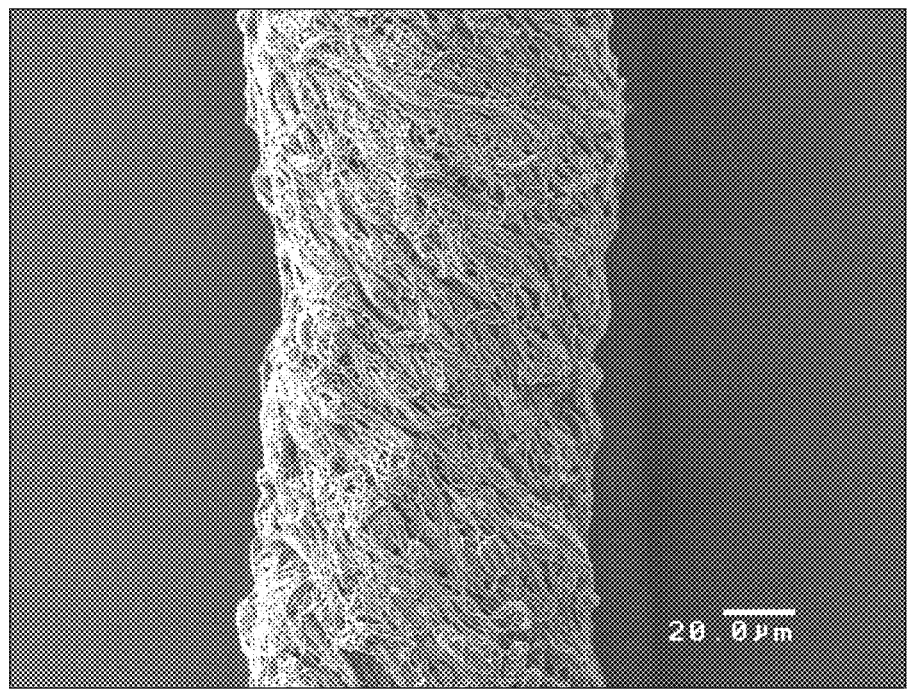
FIG. 8 shows an SEM micrograph of a fibre bundle formed using the fine mandrel method.
Figure 9:
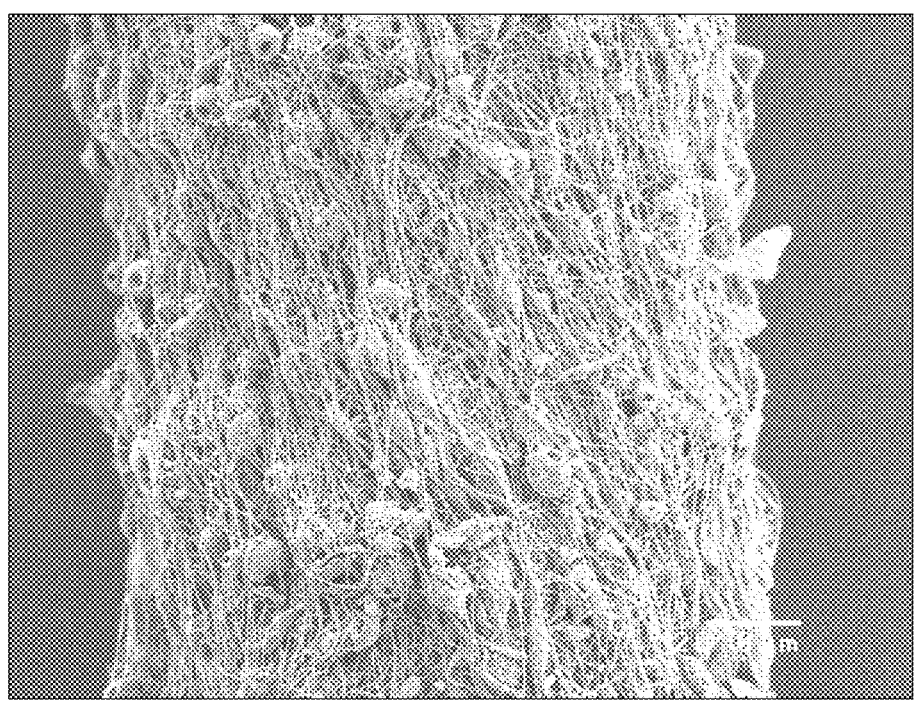
FIG. 9 shows an SEM micrograph of a fibre bundle formed using the thin mandrel method.

Bundle diameter varied depending on the fabrication technique employed: FIG. 6 shows a bundle formed using the liquid reservoir technique; FIG. 7 shows bundle formed using the fixed point technique; FIG. 8 shows a bundle formed using the fine mandrel technique; and FIG. 9 shows a bundle formed using the thin mandrel technique. The broadest bundles were fashioned from the thin edged mandrel and the thinnest from the liquid reservoir method.

The diameter of the fibres contained within each bundle ranged from submicron to micron (see Table 1) and averaged 1 µm in diameter for three of the four methods—FP, FM and TM. Fibres within LR bundles were submicron in diameter. Indeed, fibres having diameters as low as 200 nm have been produced using the techniques described herein.

TABLE 1

| Bundle formation method | Average fibre diameter within each bundle (µm) (±St Dev) | Average bundle diameter (µm) (±St Dev) |
| --- | --- | --- |
| Liquid Reservoir | 0.64 (±0.19) | 46.84 (±16.89) |
| Fixed Point | 1.06 (±0.31) | 144.22 (±49.26) |
| Fine Mandrel | 1.03 (±0.28) | 189.83 (±15.84) |
| Thin Mandrel | 0.98 (±0.28) | 375.47 (±71.91) |

The diameter of the created bundle was dependent on the chosen method, which followed the trend from large to small: TM>FM>FP>LR. Bundles formed by the TM technique were approximately eight times wider in diameter compared to LR bundles, and is due to the wide edged area for fibre coverage of the mandrel compared to a fine needle-tip to draw off fibres.

The presence of beads in amongst the fibres could be the result of coiled polymer chains that have not been sufficiently stretched during the electrospinning process prior to their impact on the collector.

With the same electrospinning parameters being applied to each collection method, it might be expected that individual fibres contained within the bundles would be of similar diameter. However, the fibres within the LR bundles were finer, compared to the other three methods whose fibres were very similar. The difference for fibres within the LR bundles may be due to the drawing of fibres from the liquid reservoir surface, which causes them to stretch and thin as the liquids surface tension has to be overcome in order for the fibres to be removed.

SEM—Secondary Bundles

Figure 10:
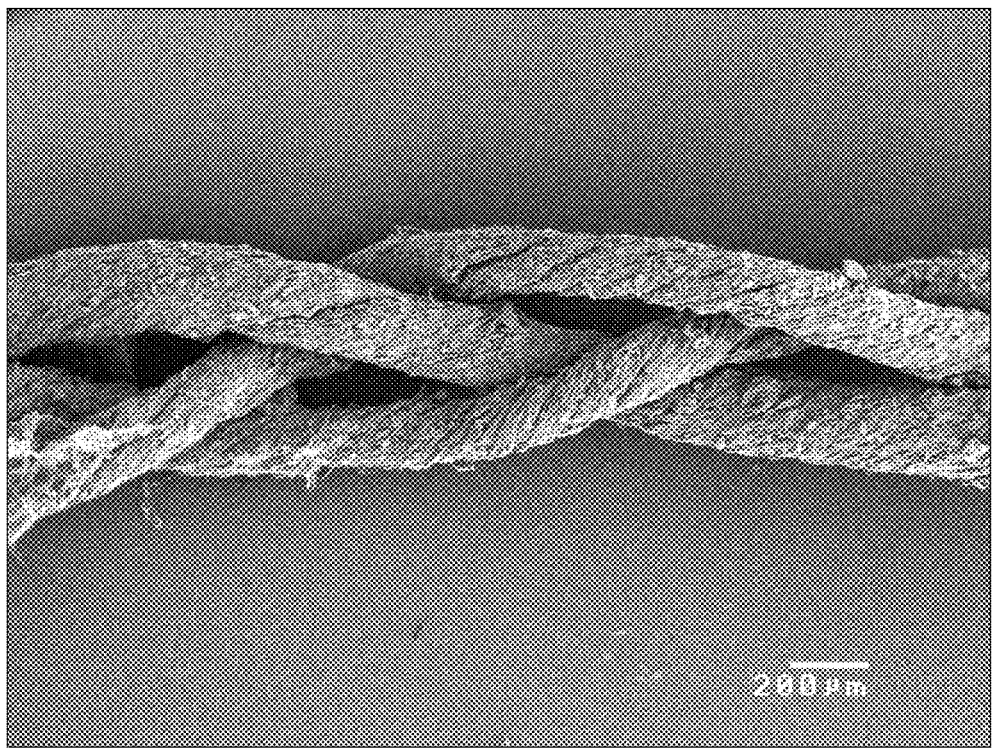
FIG. 10 shows an SEM micrograph of a secondary fibre bundle formed by plaiting a plurality of primary fibre bundles.

SEM images of secondary bundles, formed from primary bundles spun from the fine mandrel, showed the desired plaited and twisted configurations. FIG. 10 shows the plaited configuration. Three primary fibre bundles have been plaited to form a secondary bundle. Other numbers of primary fibre bundles could be used, for example five or more.

Figure 11:
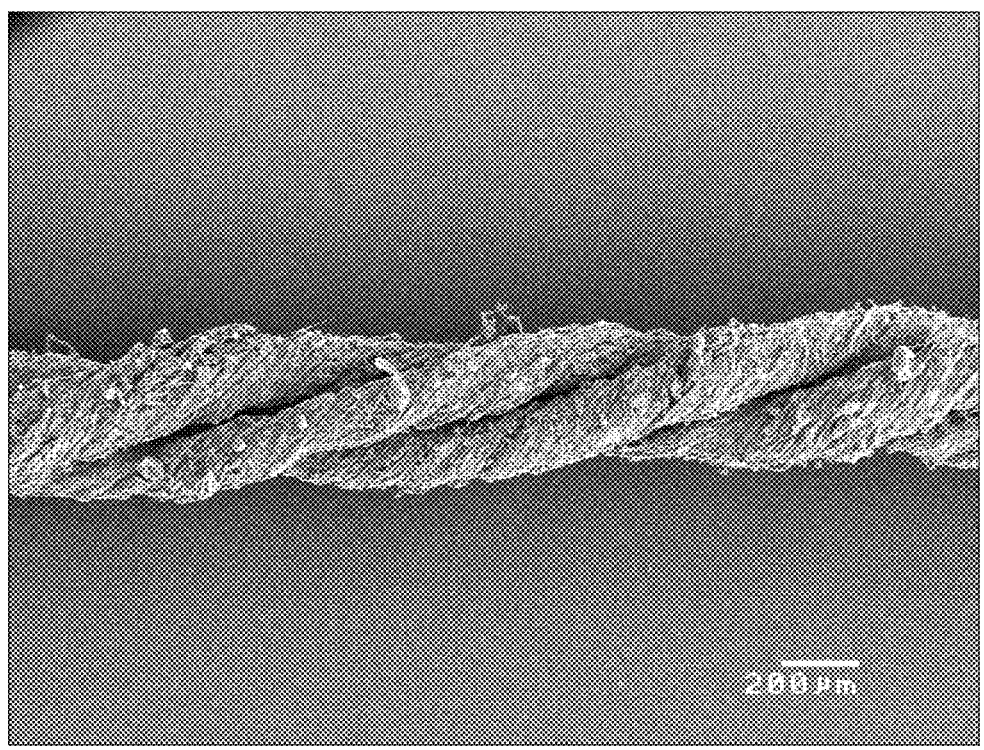
FIG. 11 shows an SEM micrograph of a secondary fibre bundle formed by twisting a plurality of primary fibre bundles.

FIG. 11 shows the twisted configuration. Three primary fibre bundles have been twisted to form a secondary bundle. Other numbers of primary fibre bundles could be used, for example five or more.

SEM—Tertiary Bundles

Figure 36:
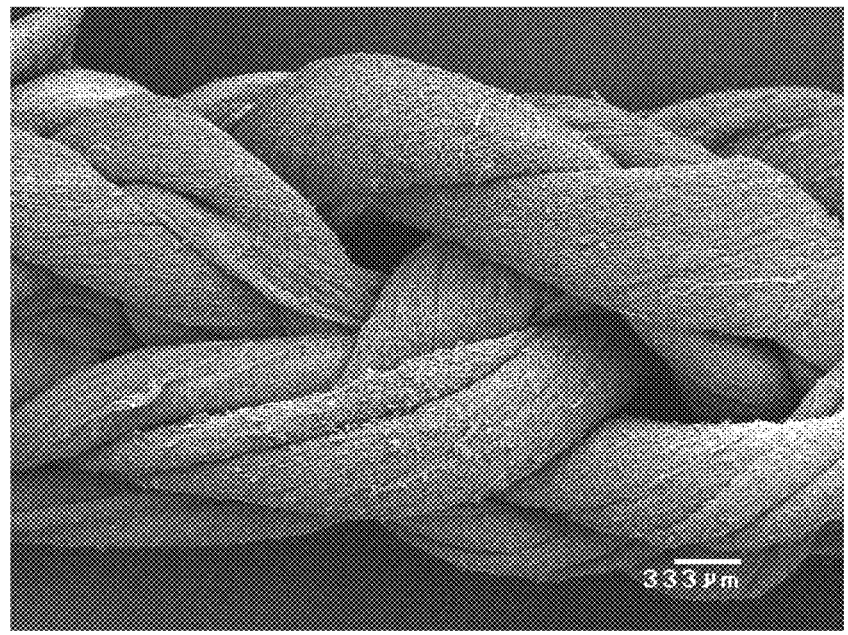
FIG. 36 shows an SEM micrograph of a tertiary fibre bundle comprising 3 inter-twined secondary bundles.
Figure 37:
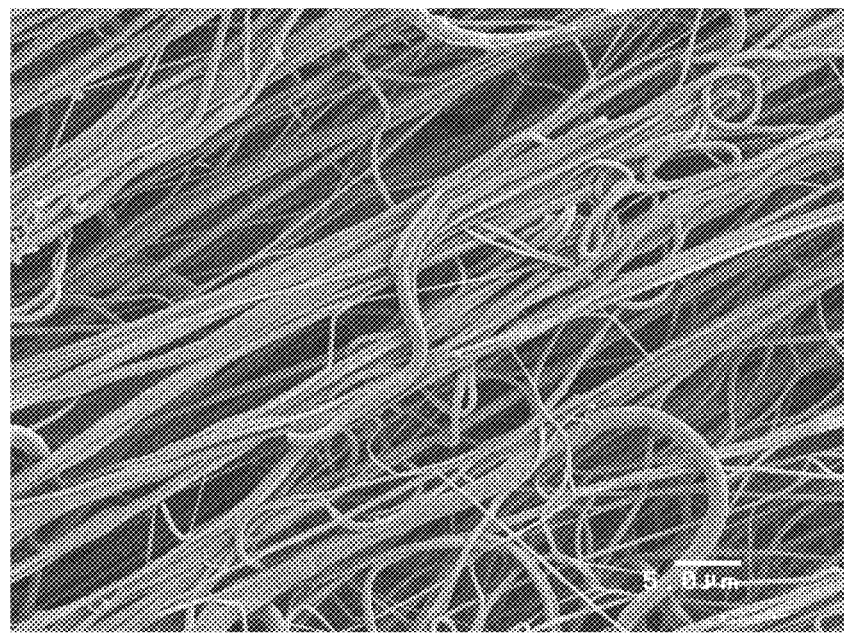
FIG. 37 shows an SEM micrograph of an enlarged area of the tertiary fibre bundle of FIG. 36.

SEM images of tertiary bundles, formed by plaiting secondary bundles of the sort discussed above, are shown in FIGS. 36 and 37. FIG. 37 shows the individual PCL fibres in an enlarged area of the scaffold of FIG. 36. In this example, 3 secondary bundles are combined, however more than 3 secondary bundles can be combined if desired. The overall diameter of the tertiary structure shown in FIG. 36 is 2.37 (+/−0.09) cm.

(4) Degradation Tests

Fibre bundles obtained using the methods set out above were subjected to a 3 month in vitro degradation study to ascertain rate of degradation and to identify degradation products.

A three month degradation study was performed on PCL electrospun 2D aligned-fibrous mats, 3D fibrous bundles and solvent cast films. All samples were fabricated from one solution of PCL dissolved in Acetone at a concentration of 10% w/v. The two electrospun sample types were collected from a rotating mandrel (diameter 120 mm, edge thickness 3 mm) (500 RPM); spinning time was 15 minutes.

The 3D bundles were created as described above in respect of the FM and TM methods. To replicate sample length, mats were cut every 3 cm along the length of the single collected fibrous strip.

All samples were fabricated on the same day and individually suspended in eppendorfs (Fisherbrand) containing 1.5 ml sterile Phosphate Buffer Solution (PBS) (Invitrogen). All eppendorfs were covered in lab-film and housed within a 37° C. oven (Binder). The degradation study was performed for 3 months; at each time-point, samples were taken from the oven, the PBS was removed and samples were left to dry prior to testing.

The mechanical properties (Young's modulus, tensile stress and maximum strain) of the fibre bundles were measured during 3 month period. Similarly, GPC, HPLC and electrospray-MS was used to identify the degradation products. DSC measurements were used to monitor the degradation of the fibre bundles.

GPC samples were separately dissolved in Tetrahydrofuran (Fisher Scientific) (concentration 0.2% w/v). 100 pl of solution was injected into the GPC, which had been calibrated with polystyrene (PS) (Pressure chemical standards) standards in THF with known molecular weights ranging from 600–7.7×106. Distilled THF with flow rate 1 ml/min was used as the mobile phase. The mobile phase and pump delivers the sample to the column and ensures constant solvent flow. The column (Phenomenex) was composed of Phenogel 5 µm, with pore sizes 500 Å, 5×104 Å and 5×106 Å.

Data acquisition and analysis was achieved with PSS Win GPC software, which allowed average molecular mass and polydispersity index to be determined. Testing was performed in triplicate and mean molecular mass distributions analysed for each sample type.

For the HPLC analysis, the column used was a reverse phase column, with nucleosil packing material with pore size 100 Å, particle size 5 µm, column length 250 mm and diameter 4.6 mm (Macherey Nagel). The column was set-up with 1 ml/min with a gradient from 20% Buffer B (acetonitrile with 0.1% tri-fluoroacetic acid) to 80% Buffer B over a period of 31 minutes. Buffer A was HPLC grade water with 0.1% trifluoroacetic acid. All concentrations for calibration curves were made up in 20% Buffer B and 80% Buffer A.

The results of the degradation test confirmed that the PCL fibre bundles continued to provide a mechanical function (as would be desirable in the case of the repair of certain tendons) and that the degradation products are oligomers and lactones, which would not be toxic to a patient.

Thermal Analysis

A heat flux differential scanning calorimeter (DSC Q100 TA) with auto-sampler and refrigerated cooling system was used to analyse the spun bundles. Collated data was analysed using software Universal Analysis 2000 v.4.2E from TA Instruments. The first heat was used to determine whether the processing technique applied to the electrospun fibres had any effect on the materials melting point and crystallinity.

Percentage crystallinity was calculated from the heat of fusion and a 100% crystalline PCL with a fusion enthalpy of 135.44 J/g was used as a reference [Crescenze V. et al 1972].

The DSC results are shown in Table 2. They showed a variation in melt enthalpy between bundle types, subsequently affecting bundle crystallinity. The melting point of the PCL depended on bundle method used. LR bundles resulted in lowest melting point. Highest crystallinity was observed from FM bundles and was similar to the crystallinity obtained for commercially available (unprocessed) PCL, which was analysed as supplied.

TABLE 2

| Bundle Type | Melting point $T_m$ (° C.) | Enthalpy of fusion $\Delta H_m$ (J/g) | Crystallinity X (%) |
|---|---|---|---|
| Liquid Reservoir | 54.94 (±0.09) | 34.04 (±15.14) | 25.13 |
| Fixed Point | 55.16 (±0.30) | 40.94 (±8.27) | 30.23 |
| Fine Mandrel | 57.07 (±0.04) | 73.24 (±8.39) | 54.08 |
| Thin Mandrel | 55.40 (±0.16) | 53.49 (±12.48) | 39.49 |
| PCL (unprocessed) | 63.47 (±0.51) | 75.68 (±1.62) | 55.88 |

Polymer crystallinity appears to be dependent on the bundle fabrication method and follows the trend FM>TM>FP>LR, with FM being most crystalline and LR least. FM bundles demonstrated a crystallinity of 54.08% when compared to fully crystalline PCL. However, in its standard form PCL is semi-crystalline and when analysed proved to be 55.88% crystalline.

The difference in crystallinity may be due to the final molecular orientation of the polymer chains contained within the bundles fibres. The results suggest bundles fabricated from the mandrel edge are of the highest order, indicating greater orientation within the fibres and liquid reservoir bundles of the lowest order as fibres were initially spun in a random arrangement before being purposefully aligned. Altered molecular orientation is further supported by a similar change in bundle melting temperature as a more ordered structure requires greater energy to melt.

Crystallinity is affected by the molecular orientation within the bundle fibres and this influences the materials mechanical properties. The mechanical data re-iterates this variation in bundle crystallinity. Higher crystalline structures tend to be more brittle, having lower tensile strength and modulus, despite undergoing significant deformation.

During the 3 month degradation study, PCL samples demonstrated increased crystallinity, suggesting hydrolytic attack had occurred within the amorphous regions of the polymer, and caused the rearrangement of chains to create a more ordered structure. Analysis of the first heat cycle for all samples during the degradation study demonstrated similar trends in melting temperature and Enthalpy of Fusion: the melting temperature increased over time and the Enthalpy of Fusion resulted in an overall increase after three months.

An increase in modulus and tensile strength was also observed during the 3 month study, with the highest values for modulus and tensile strength being observed at the 3 month point. Thus, the change in crystallinity gives rise to a favourable change in the mechanical properties of the scaffold.

In a longer study, the observed level of crystal formation appears to be limited in that once a maximum has been reached, degradation of the oligomers and breakdown of the crystals can be expected.

The observed variation in the crystallinity and hence mechanical properties of the PCL fibre bundle scaffold may provide a further advantage in tendon repair: an increase in mechanical properties in the first few months after insertion, followed in later months by a reduction in mechanical properties to coincide with growth/repair of the tendon. In this way, the fibre bundle scaffold suitably provides time-dependent replacement of the function of the natural tissue.

(5) Mechanical Testing of Scaffold

Young's Modulus, Tensile Strength and Maximum Strain

Bundles were secured to cardboard strips, allowing adequate gripping in the tensile tester clamps. Fibres were acclimatised to testing room conditions (23° C., 50% RH) for 24 hours prior to their testing with an Instron, with 5 N load cell and 5 mm/min crosshead speed.

Young's modulus was calculated for each fibre bundle using the same two strain points to enable direct comparison between bundles. Ultimate tensile strength was recorded as the highest stress (MPa) withstood by the bundle prior to breakage. Maximum strain, being the elongation or change in length of the bundle, was measured at the point of total bundle breakage.

Figure 12:
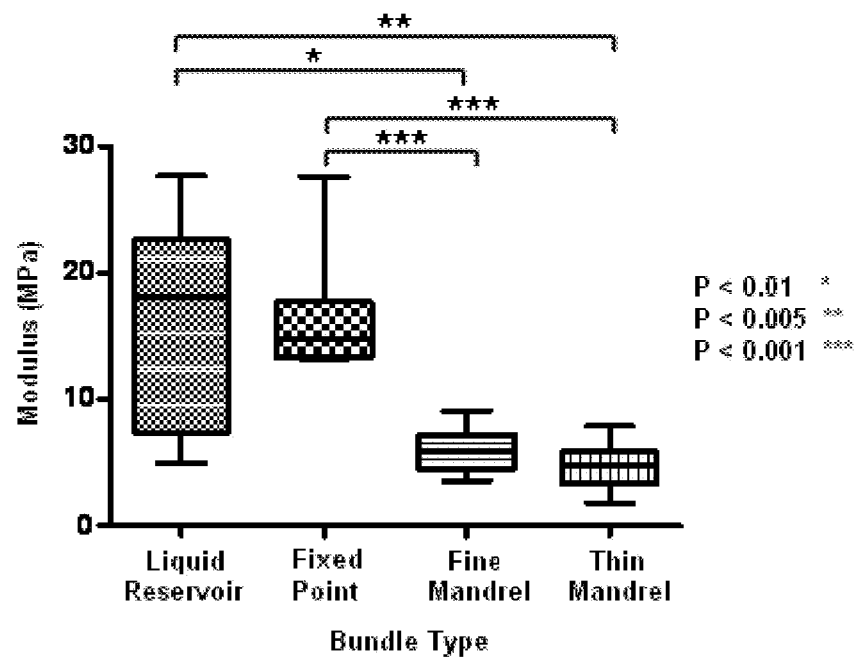
FIG. 12 shows the results of the Young's modulus measurements.
Figure 13:
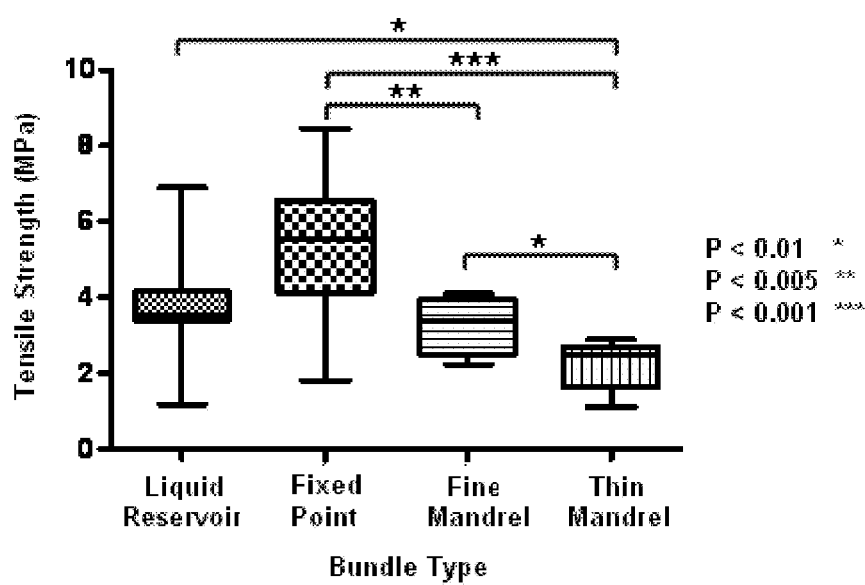
FIG. 13 shows the results of the tensile stress measurements.
Figure 14:
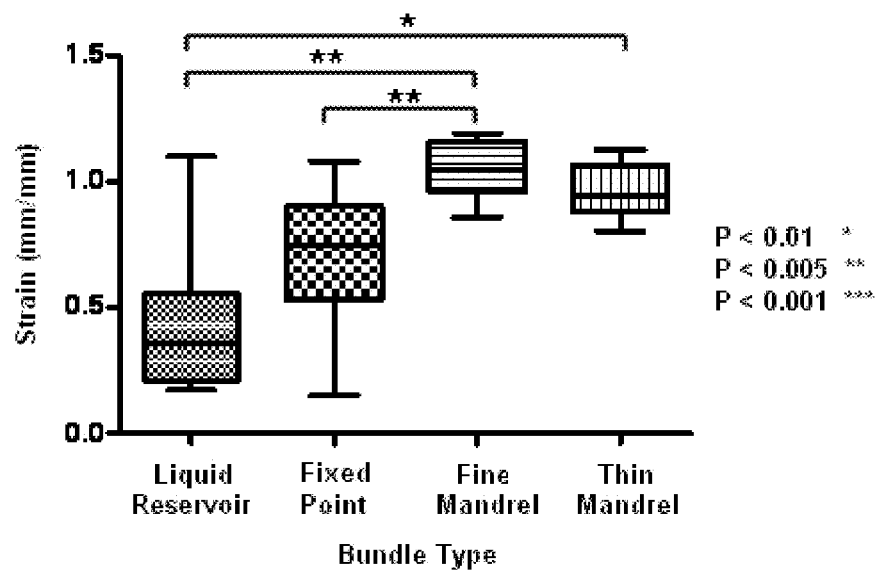
FIG. 14 shows the results of the maximum strain measurements.

Mechanical data are represented in FIGS. 12 to 14 as box and whisker plots. Each bundle group is represented by the median and inter-quartile range (boxes), and the maximum and minimum values recorded (whiskers). Mann-Whitney U test was used to compare Young's modulus, tensile strength and strain between different bundles types.

The results of the Young's modulus measurements are shown in FIG. 12. The stiffness of PCL was affected by the method of fabricating the bundle. Young's modulus was highest for LR bundles (16.64 MPa). However, statistical analysis showed that LR bundles were not significantly different to FP bundles. Bundles formed from either mandrel technique resulted in significantly lower modulus values compared to FP and LR bundles.

The results of the tensile strength measurements are shown in FIG. 13. Ultimate tensile strength (UTS) of bundles was highest for those created by the FP method (5.32 MPa). However, FP bundles were not significantly different to LR bundles. Variability between samples was small for both mandrel techniques. TM bundles achieved the lowest UTS.

The results of the maximum strain measurements are shown in FIG. 14. The most extendable bundles were those created by the FM method, with loaded bundles doubling in length before rupture. Lowest strain was observed with LR bundles (0.44 mm/mm). Both LR and FP bundles were significantly different compared to the FM data.

In terms of tensile strength and modulus, the results for each fabrication method are dependent on bundle diameter. Bundles of smaller diameter resulted in greater tensile strength and modulus compared to those of larger diameter. Generally, bundles achieved highest tensile strength and modulus, in the following order: FP>FM>TM.

Greatest extensibility was achieved from bundles created using the mandrel, with almost all FM bundles reaching strains of more than 100%. FP bundles displayed good extensibility, attaining >50% strain. Strain was lowest for LR bundles. This may be due to a lack of beads present within its structure, providing limited uncoiling of polymer chains that could otherwise help to endure greater strains. The lack of twist in the bundle structure and their fragility may also contribute to the poor strain properties associated with the liquid reservoir method. The results suggest bundles with a minimum number of fibres would assist in the ability to withstand the forces applied; the other bundles contained a larger number of submicron to micron fibres, providing a greater area for load dissipation, subsequently increasing bundle extension before eventual rupture.

Effect of Twist 2D electrospun mats of aligned PCL fibres were held static at one end and the other end twisted a set number of twists in the "S" direction. A counter was used to record the number of twists applied.

The twisted primary bundles were then tested using the methods discussed above to obtain values for modulus, tensile strength and strain. The measured data was analysed by one-way ANOVA and Bonferroni post tests. The results of the measurements are set out in FIGS. 38 to 40. As can be see n from the graphs, the data suggests that modulus and tensile strength are increased with increasing number of twists. A significant level of strain is observed in all cases.

Figure 38:
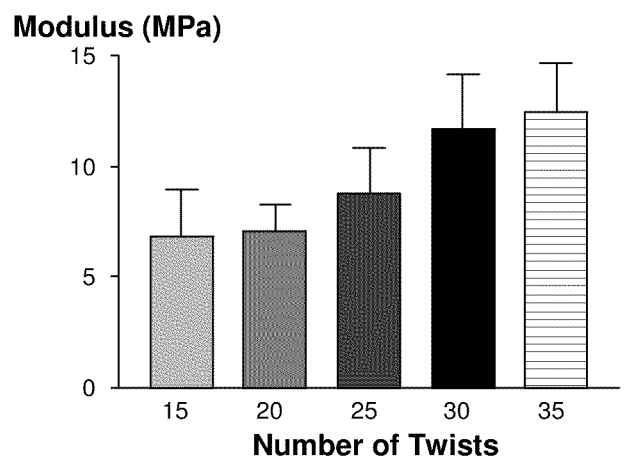
FIG. 38 shows the results of modulus measurements made on twisted bundles of aligned fibres, wherein the extent of twist is altered.
Figure 39:
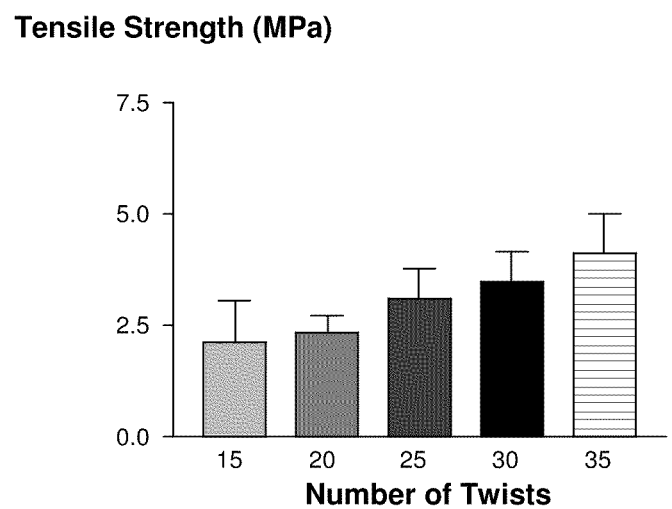
FIG. 39 shows the results of tensile strength measurements made on twisted bundles of aligned fibres, wherein the extent of twist is altered.
Figure 40:
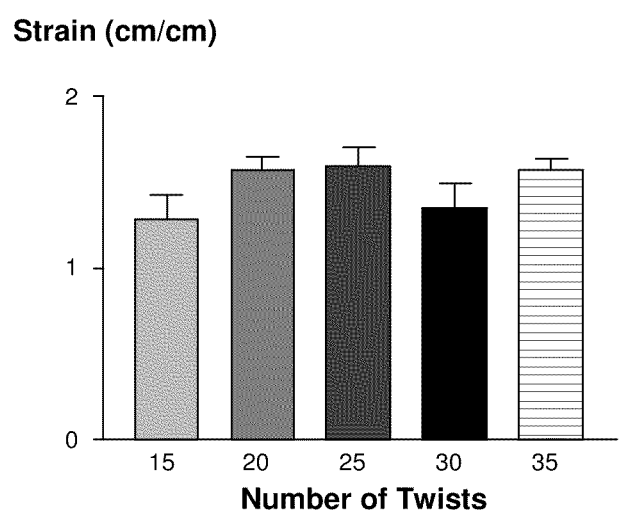
FIG. 40 shows the results of strain measurements made on twisted bundles of aligned fibres, wherein the extent of twist is altered.

Note that the number of twists reported in FIGS. 38 to 40 are twists per 3 cm of PCL fibre bundle. This can be converted to turns per metre as follows:

15 twists/3 cm=500 turns per metre 20 twists/3 cm=667 turns per metre 25 twists/3 cm=833 turns per metre 30 twists/3 cm=1000 turns per metre 35 twists/3 cm=1167 turns per metre These results demonstrate that improved mechanical properties are achieved, whilst maintaining good elongation performance.

(6) In vitro Tests

Fibre bundles were made according to the methods described above and used in the following studies to determine the effectiveness of the scaffolds of the present invention for tendon repair.

Tenocytes

Figure 15:
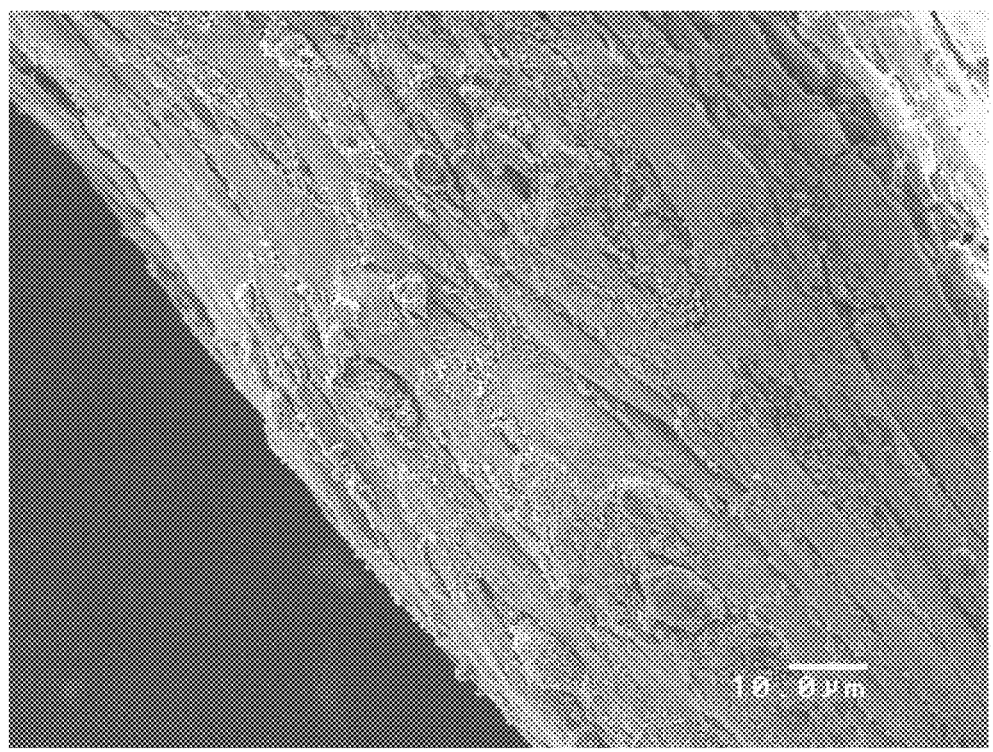
FIG. 15 shows an SEM micrograph of a fibre bundle seeded with tenocytes and after culturing.
Figure 16:
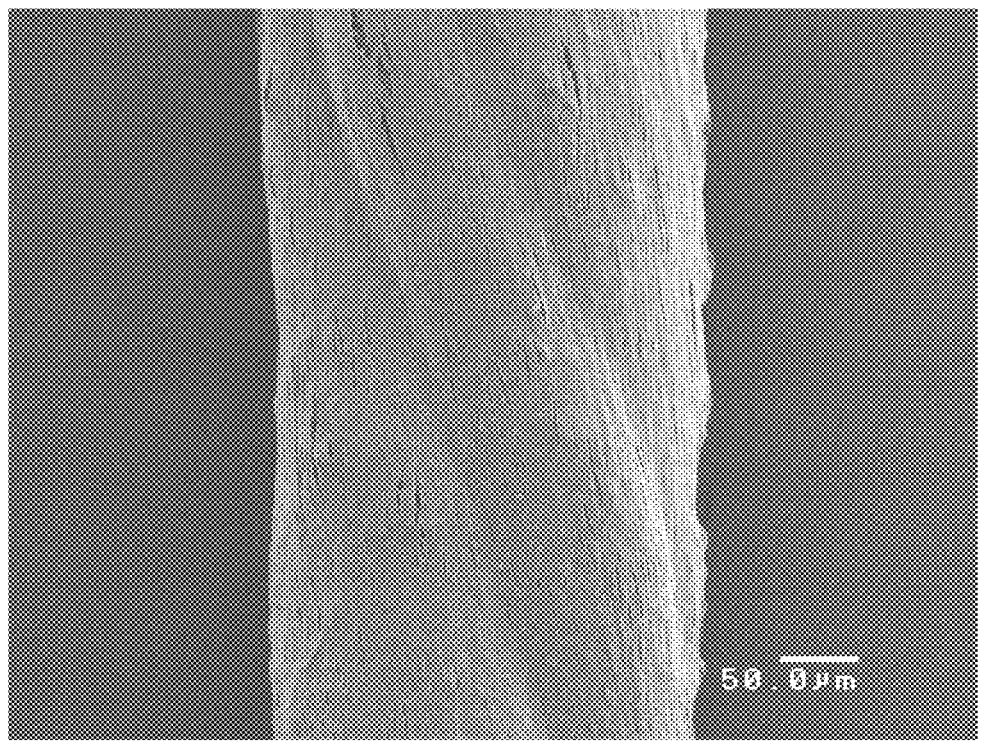
FIG. 16 shows an SEM micrograph of a fibre bundle seeded with tenocytes, with visible alignment of tenocytes after culturing.

FIGS. 15 and 16 show tenocytes seeded on primary fibre bundles having a twisted configuration. Tenocyte growth along the longitudinal axis of the scaffold is observed, with the tenocytes exhibiting some orientation that is complimentary to the twisted configuration. In particular, cell filopodia can be seen, which demonstrates cell attachment and spreading. Cells are growing in the direction of fibre alignment.

Figure 17:
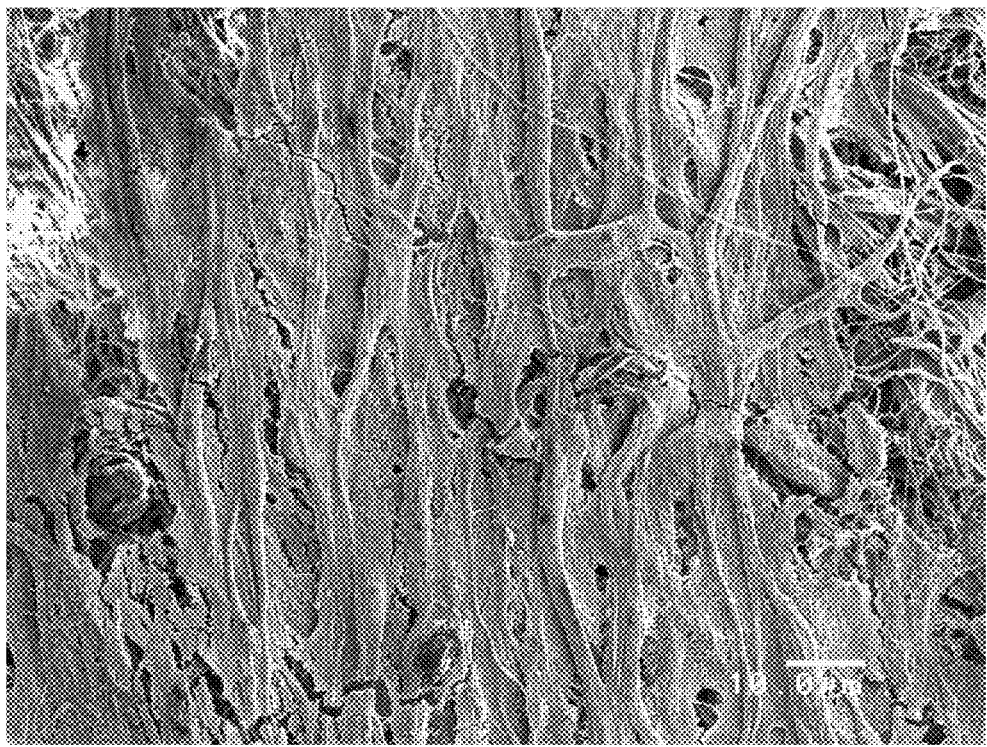
FIG. 17 shows an SEM micrograph of a fibre bundle loaded with collagen gel and seeded with tenocytes, with visible alignment of tenocytes after culturing.
Figure 18:
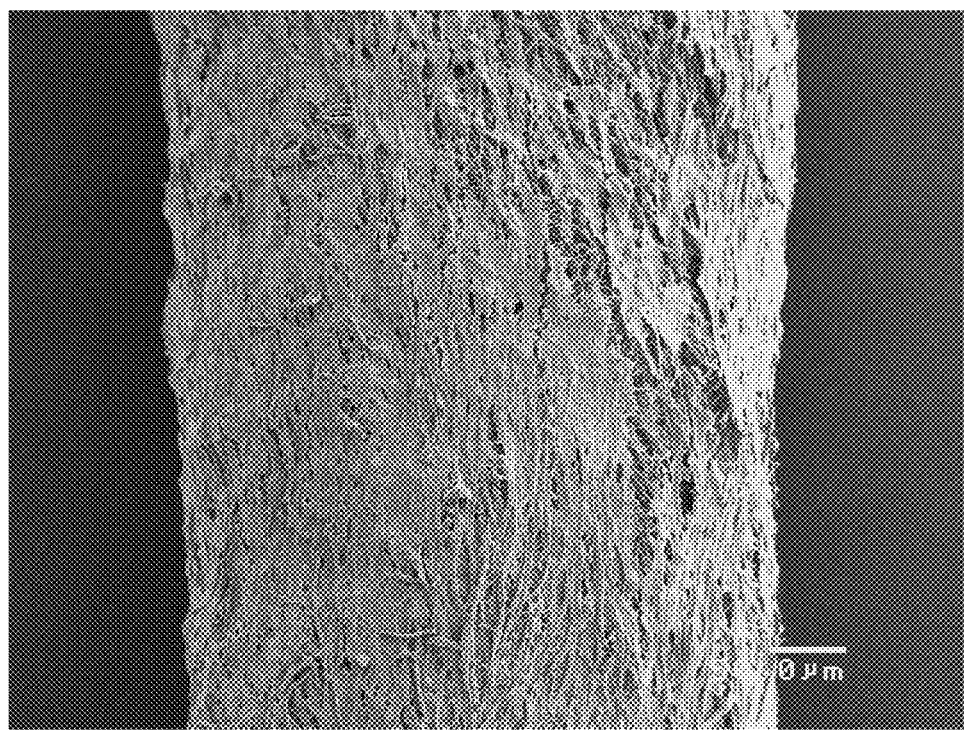
FIG. 18 shows an SEM micrograph of a fibre bundle loaded with collagen gel and seeded with tenocytes, with substantial growth of tenocytes visible after culturing.

FIGS. 17 and 18 also show tenocytes seeded on fibre bundles, but this time the scaffolds have been loaded with a collagen gel. Once again, substantial considerable tenocyte growth is observed, with growth occurring along the longitudinal axis of the scaffold. In particular, FIG. 17 is a simulation of an in vivo environment because the collagen gel provides a 3D environment to the cell which encourages the cells to "sit-up" from the surface. The cells actively moved towards the bundle and aligned along the main bundle direction. FIG. 17 shows a similar cell morphology to that which we would expect to see in vivo.

Figure 19:
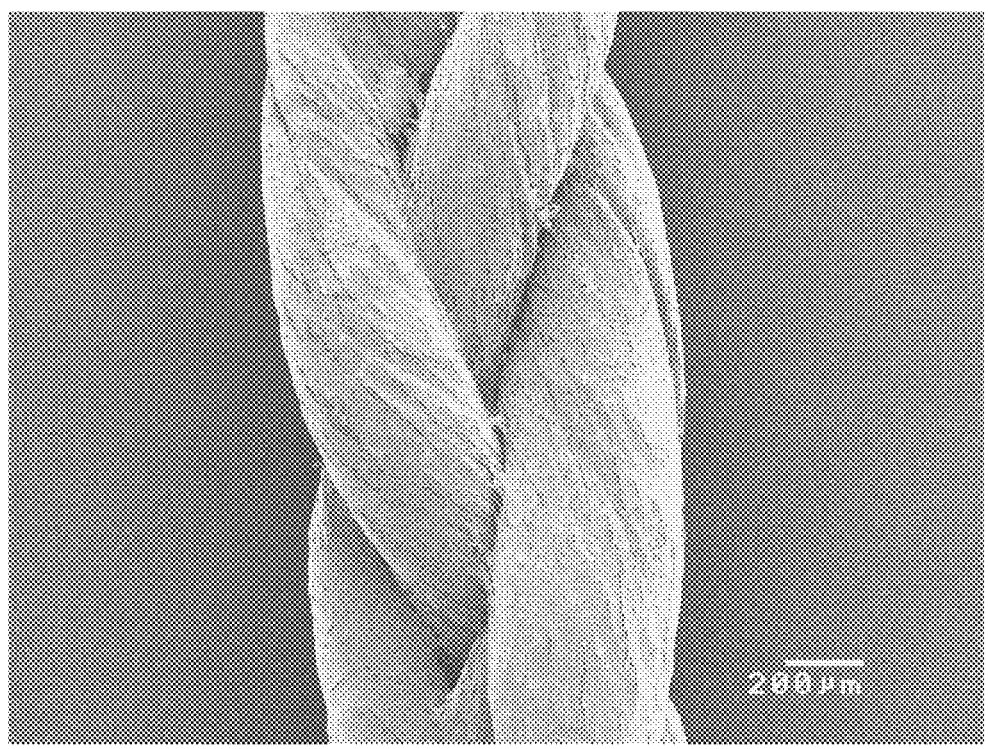
FIG. 19 shows an SEM micrograph of a plaited secondary fibre bundle seeded with tenocytes, with visible alignment of tenocytes after culturing.
Figure 20:
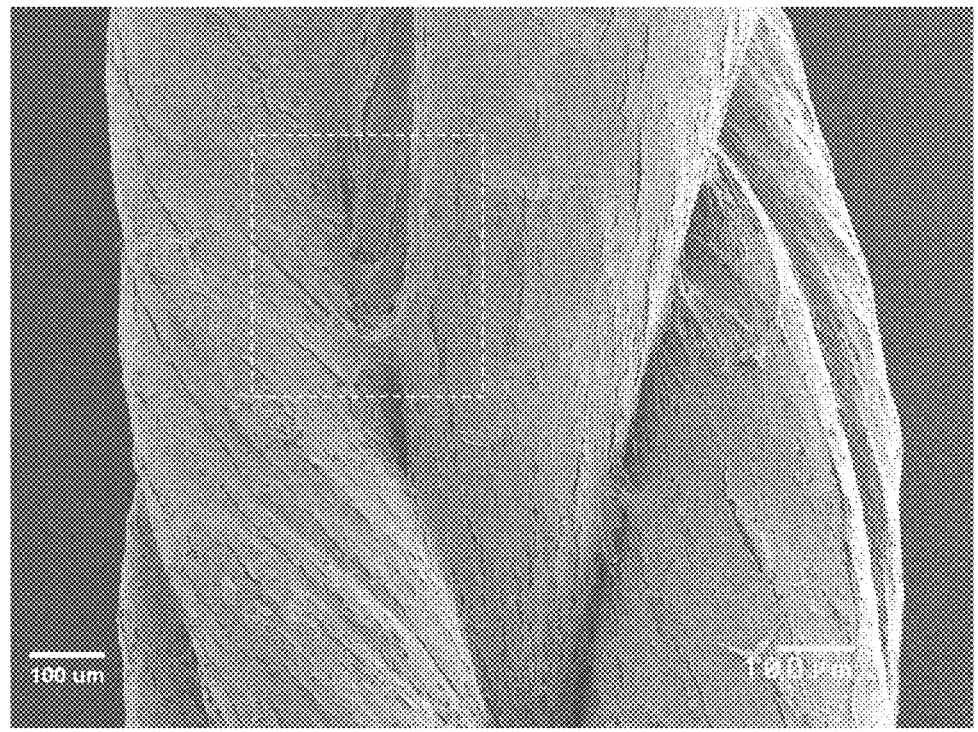
FIG. 20 shows an SEM micrograph of an enlarged area of the secondary fibre bundle of FIG. 19.
Figure 21:
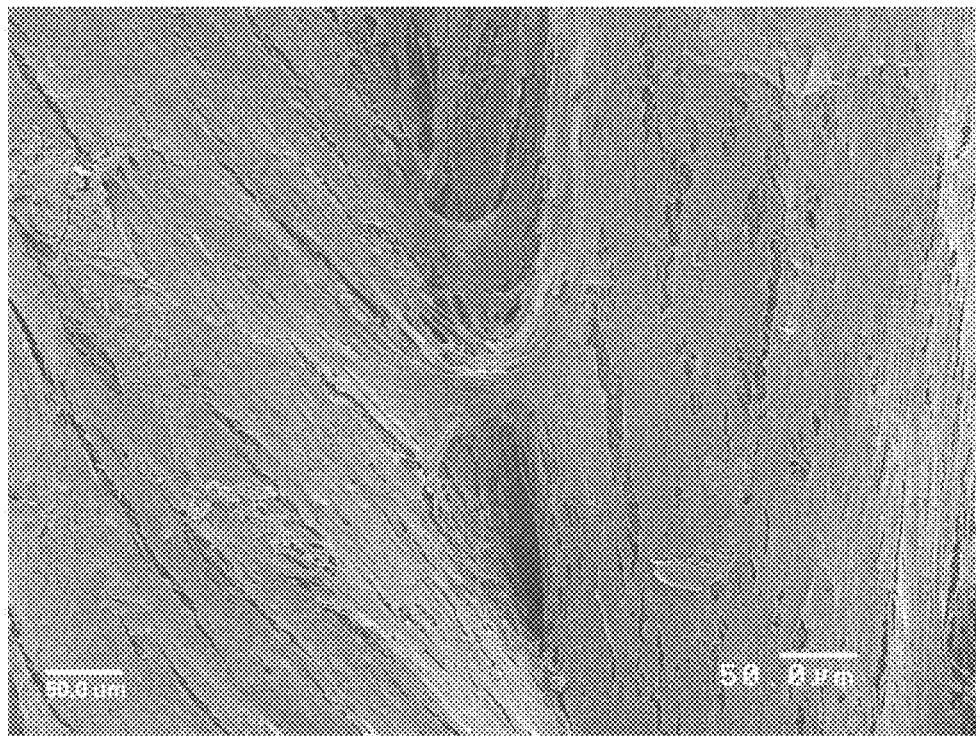
FIG. 21 shows an SEM micrograph of an enlarged area of the secondary fibre bundle of FIG. 20.
Figure 22:
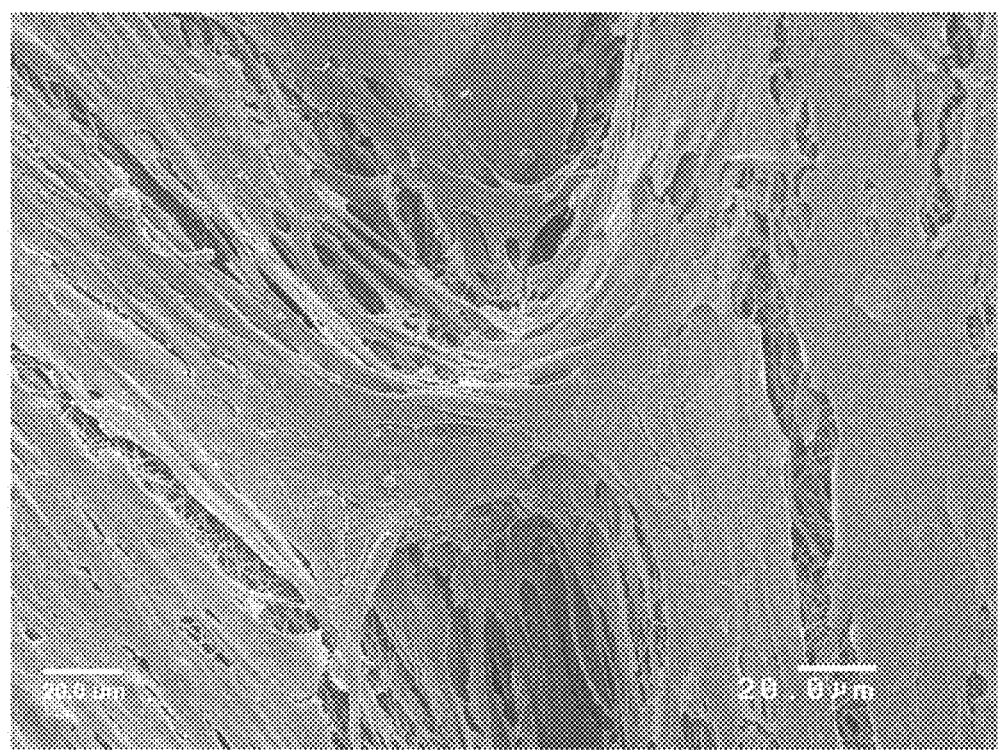
FIG. 22 shows an SEM micrograph of an enlarged area of the secondary fibre bundle of FIG. 21.
Figure 23:
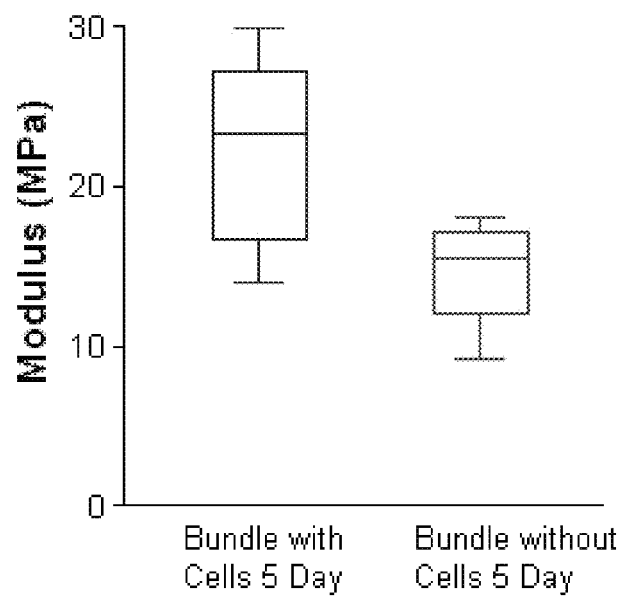
FIG. 23 shows the results of Young's Modulus biomechanical data determined for a fibre bundle cultured with and without tenocytes for a period of 5 days.

FIG. 19 shows a plaited secondary bundle onto which tenocytes have been seeded and cultured for 14 days. FIGS. 20 to 22 show close-up views of one part of the scaffold, with the region within the dashed box of FIG. 20 being enlarged in FIGS. 21 and 22. As can be seen from the micrographs, substantial tenocyte growth is observed for this plaited configuration. Of particular note is tenocyte growth within the channels between the primary fibre bundles. Similarly, a helical growth pattern is observable along the surface of the primary fibre bundles (which bundles are twisted). This suggests that tenocyte growth may be encouraged by the secondary structure of the scaffold, wherein tenocytes growth follows not only the topography of the fibres in the primary bundles but also the topography of the secondary bundles (for example, tenocytes grow along the channels formed between the primary bundles).

Cell Proliferation

Cell proliferation assays were conducted, with the results demonstrating that considerable attachment, growth and proliferation occurs on the scaffolds and aligned fibre bundles of the present invention.

Gene expression assays were also conducted using genes associated with tendon tissue development. The results of these assays confirmed that tendon tissue development was occurring in and along the scaffold. Macrophage activation studies were conducted to ascertain the biocompatibility and suitability for in vivo use of the specific structures of the present invention. The results of the studies showed that macrophages were not activated.

Effect of Cell Culture on Material Biomechanics 2D fibrous sheets and 3D bundles, prepared as described herein, were cultured for 5 days—with and without tenocytes—to determine whether the presence of cells affected mechanical properties. A time period of 5 days was chosen as SEM imaging demonstrated significant cellular alignment along the nanofibre axes and production of extracellular matrix (ECM).

For cell-seeded samples, 50,000 cells per cm$^2$ were seeded onto each of the electrospun constructs.

All samples were tested on an Instron (2211), with a crosshead speed of 5 mm/min. The data is presented in FIGS. 23 to 28 by box and whisker plots, which correspond to the median, lower and upper inter-quartile range (boxes) and the maximum and minimum values recorded (whiskers).

The results show that after culturing with cells for 5 days the mechanical properties for both 3D bundles and 2D fibrous sheets were surprisingly improved. This increase in mechanical properties may be due to the penetration of cells and ECM between the samples nanofibres, generating a composite-like material.

Figure 24:
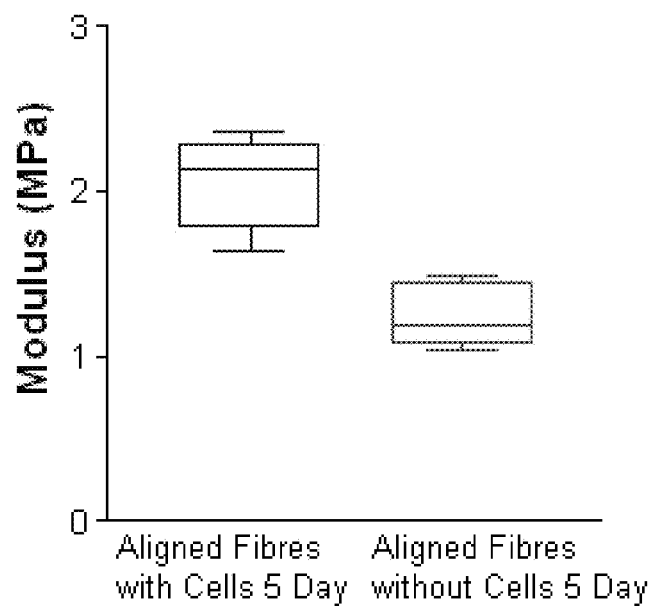
FIG. 24 shows the results of Young's Modulus biomechanical data determined for a 2D fibre sample cultured with and without tenocytes for a period of 5 days.
Figure 25:
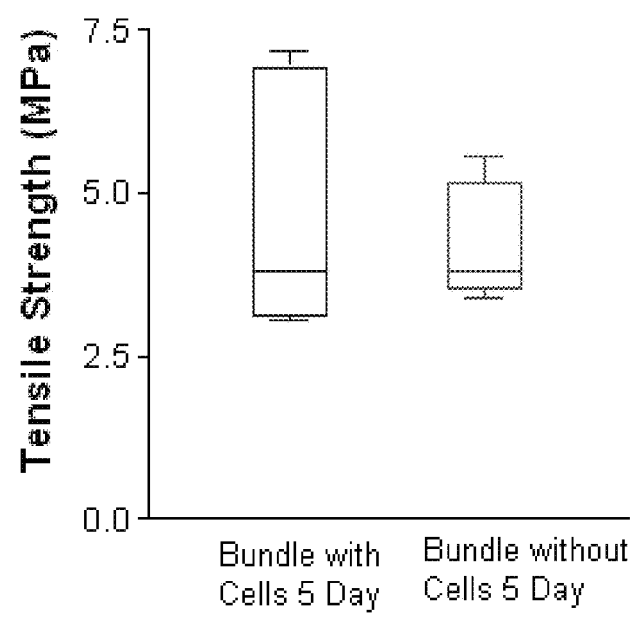
FIG. 25 shows the results of Tensile Strength biomechanical data determined for a fibre bundle cultured with and without tenocytes for a period of 5 days.
Figure 26:
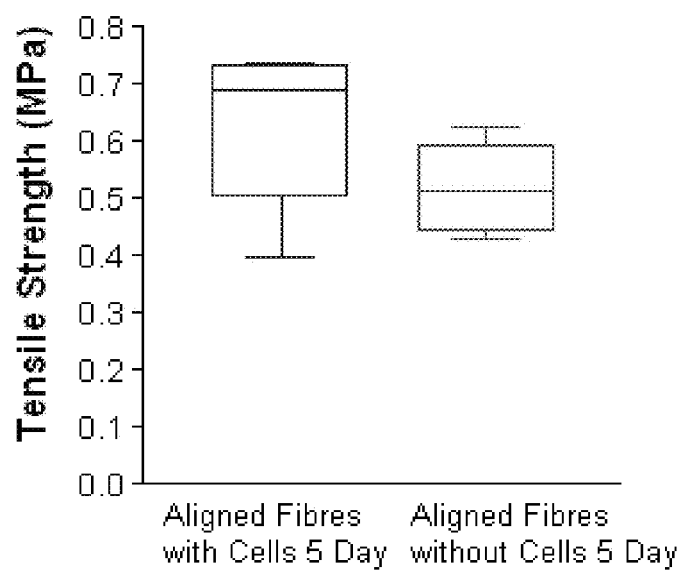
FIG. 26 shows the results of Tensile Strength biomechanical data determined for a 2D fibre sample cultured with and without tenocytes for a period of 5 days.
Figure 27:
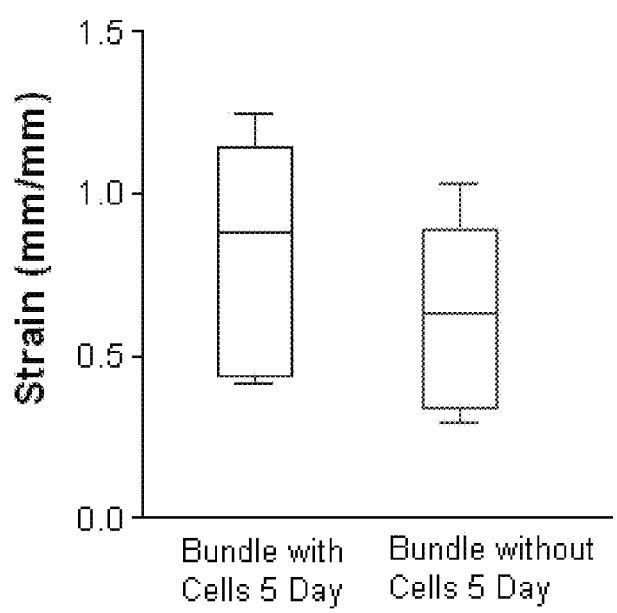
FIG. 27 shows the results of Maximum Strain biomechanical data determined for a fibre bundle cultured with and without tenocytes for a period of 5 days.
Figure 28:
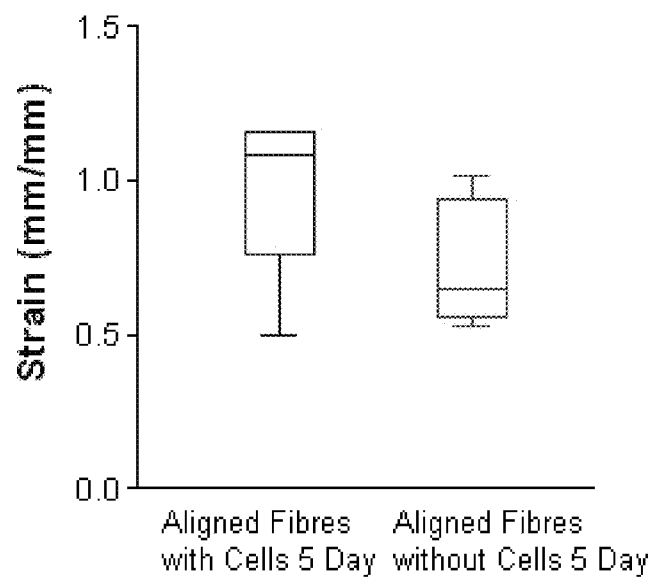
FIG. 28 shows the results of Maximum Strain biomechanical data determined for a 2D fibre sample cultured with and without tenocytes for a period of 5 days.

These results also demonstrate the significant advantage achieved in terms of mechanical properties by the 3D fibre bundles (FIGS. 23, 25 and 27) as compared to the 2D fibres (FIGS. 24, 26 and 28). In this connection, whilst the dimensions of the 3D bundles do not represent the tendon as a whole, it is intended that the mechanical properties of the scaffold will be adjusted depending on the level of damage sustained to the tissue, in terms of the number of bundles required to fill the void and the chosen weaving technique employed. The scaffold is intended to promote new tendon tissue formation and provide adequate mechanical properties, ultimately reducing patient recovery time.

(7) In vivo Tests

Mouse Model

A preliminary pilot study using six C57BL/6 male mice between 8-12 weeks old was undertaken. The mice were supplied from the animal facility at the University of Manchester. Two mice were harvested per time-point (0, 3 days and 3 weeks).

Figure 29:
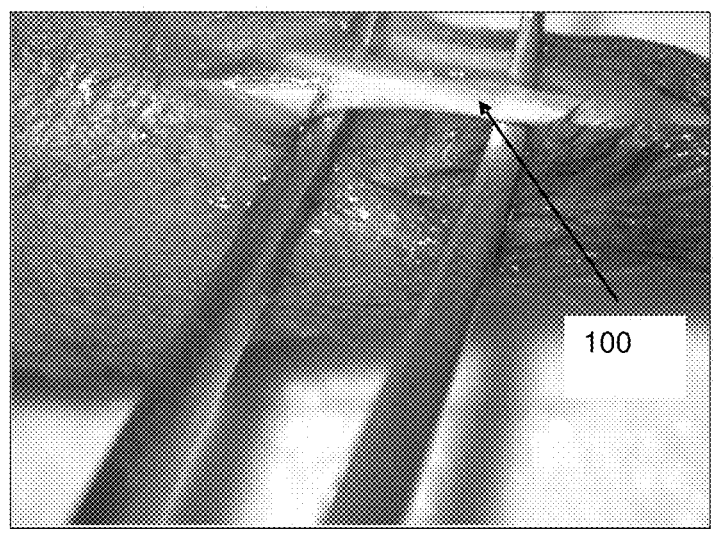
FIG. 29 shows a mouse Achilles tendon exposed through a mid-posterior incision.
Figure 30:
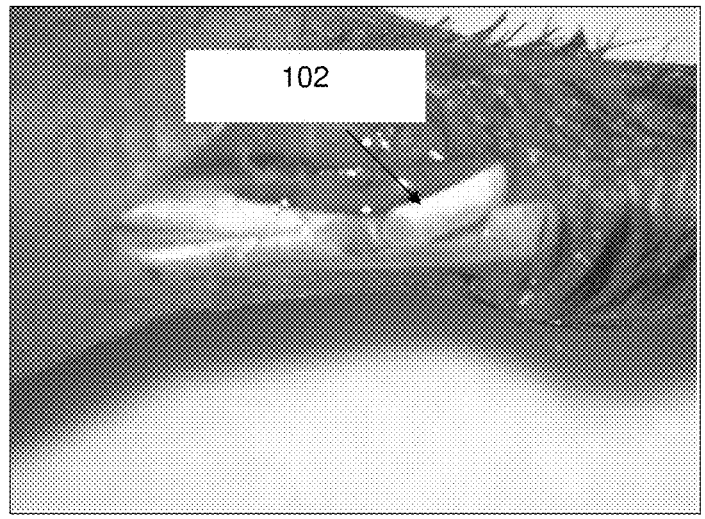
FIG. 30 shows the mouse tendon of FIG. 29 with the excised section of the Achilles tendon removed.

The operating room was set up as appropriate and mice anaesthetised. Their legs were shaved and hair removed. A tourniquet was applied around the thigh and longitudinal incision made at the mid-posterior line from the musculo-tendinous junction down to the ankle joint. The Achilles tendon was identified (see 100, FIG. 29) and 50% of the tendons width and 4 mm longitudinally excised (see 102, FIG. 30).

Figure 31:
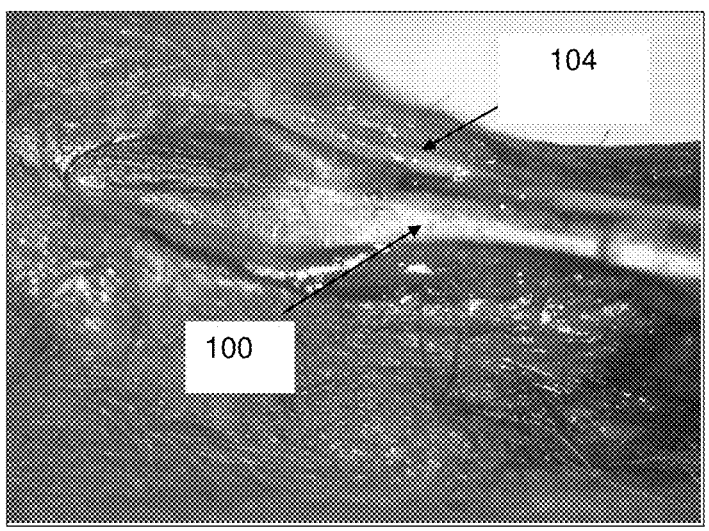
FIG. 31 shows the mouse tendon of FIG. 30 with a fibre bundle scaffold of the present invention lying next to the Achilles tendon.
Figure 32:
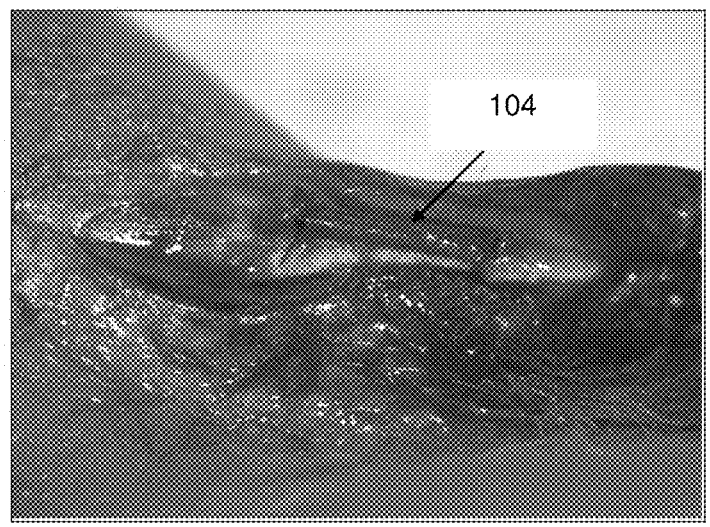
FIG. 32 shows the mouse tendon of FIG. 31 with the fibre bundle scaffold grafted into the Achilles tendon and sutured at either end.

The scaffold, prepared as described herein, was grafted into the defect and sutured with polyamide sutures (Braun Medical, UK) proximally and distally (see 104, FIGS. 31 and 32). Throughout the operation, the tendon was kept well hydrated by regular irrigation with saline. The tissue was returned to its original position and the skin closed with sutures. The total procedure time for each mouse was 90 minutes. The mice were weighed and kept in individual cages.

All mice survived the surgery and continued to eat and drink well. Mice were followed up daily for the first three days post-surgery and then weekly until harvest. Weight, ambulation and wounds were recorded (see Table 3). Normal ambulation returned after 24-48 hours, which was within the expected recovery period.

TABLE 3

| Mice | Age of mice | Weight (g) | Time of harvest | Weight (g) | Postoperative period |
|---|---|---|---|---|---|
| 1 | 8-10 wks | 26.8 | Day 0 | same | None |
| 2 |  | 25 |  | same | None |
| 3 |  | 25 | Day 3 | 22.5 | Uneventful |
| 4 |  | 28 |  | 26.6 | Day 2-Swollen left leg, superficial wound dehiscence |
| 5 |  | 26.5 | Day 21 | 28.2 | Uneventful |

TABLE 3-continued

| Mice | Age of mice | Weight (g) | Time of harvest | Weight (g) | Postoperative period |
|---|---|---|---|---|---|
| 6 | | 28 | | 27 | Day one- Both legs slightly swollen Day 2- Superficial wound dehiscence over the ankle area, settled by end of first week |

The scaffolds were easy to handle during surgery, being were non-slippery and easy to suture in place. The positioning of the scaffold within the tendon tissue was found to be easy, which is an important advantage for a scaffold that is to be used in this type of surgery. Each procedure was straight forward and only one scaffold was needed for each procedure (i.e. no scaffolds were rejected by the surgeon through e.g. unsuitability, difficulty in handling, damage during handling).

Figure 33:
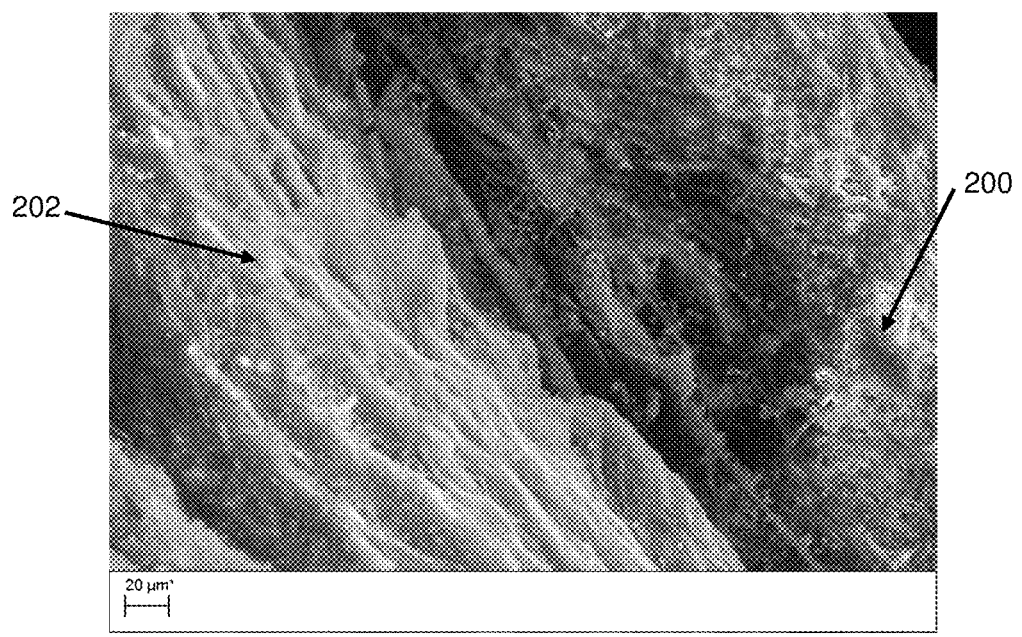
FIG. 33 shows an SEM micrograph of a mouse tendon and sutured PCL fibre bundle scaffold.
Figure 34:
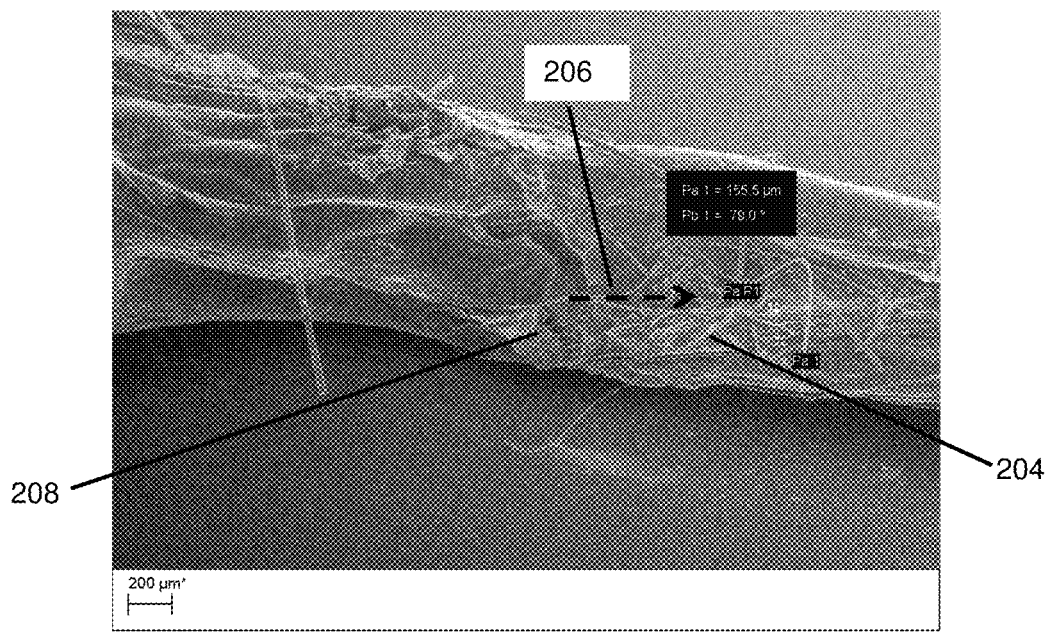
FIG. 34 shows an SEM micrograph of a mouse tendon and sutured PCL fibre bundle scaffold after 3 weeks in vivo.
Figure 35:
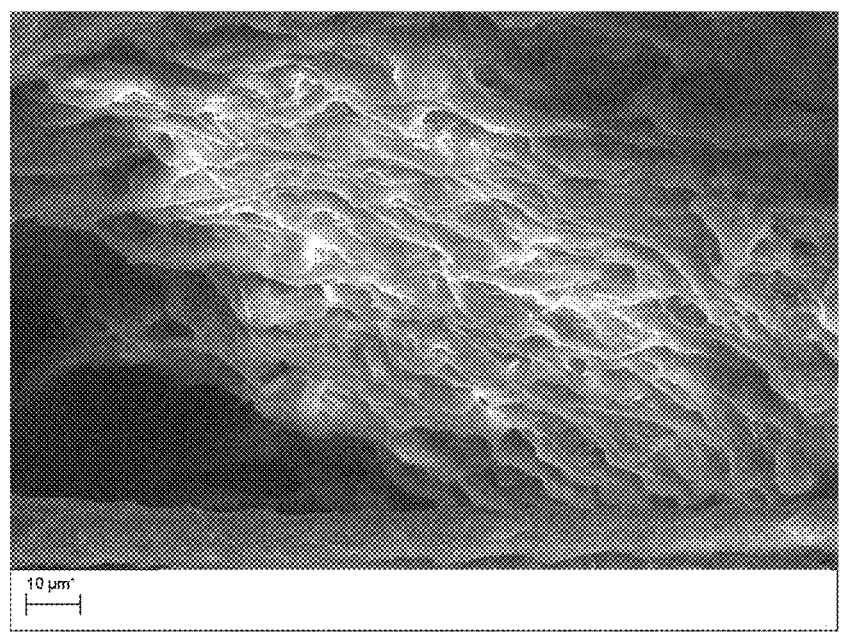
FIG. 35 shows an SEM micrograph of new tissue that has grown on the PCL fibre bundle scaffold after 3 weeks in vivo.

FIG. 33 shows a PCL scaffold 200 in-situ alongside natural mouse tendon 202 shortly after suturing. FIG. 34 shows a PCL scaffold 204 after 3 weeks in vivo. The orientation of the scaffold is indicated by dashed arrow 206. The location of the suture is shown at 208. FIG. 35 shows new tendon tissue growth on the PCL fibre bundle scaffold after 3 weeks in vivo.

It is clear from these SEM micrographs that the PCL fibre bundle scaffold has a similar morphology to the natural tendon and that substantial tendon cell growth occurs in vivo.

This positive preliminary pilot study indicates that scaffolds comprising PCL fibres represent a successful method for the repair of damaged tendons.

The examples described herein demonstrate that 3D bundles containing electrospun PCL fibres can be fabricated so as to control fibre diameter, bundle diameter and morphology. For example, the overall diameter of the bundle can be adjusted by appropriate selection of the processing method: the affect on diameter being as follows: TM>FM>FP>LR (largest to smallest).

LR and FP bundles resulted in the highest Young's modulus. Tensile strength was greatest for FP bundles. Maximum strain was achieved with bundles made from the FM method.

Whilst the mechanical properties of tendons are considerably higher when compared to the bundles tested in this study, a single bundle is representative of only one small part of the overall tendon structure. It is proposed that the extent of tissue damage incurred will determine what size scaffold is required. Development of a larger construct would involve inter-weaving several bundles together, which should improve mechanical properties and further replicate tendons natural hierarchical structure.

The processing technique applied to the electrospun fibres appears to affect material crystallinity and melting point, with observed crystallinity being in the following order: FM>TM>FP>LR. Melt onset temperature follows the same trend.

The scaffold architecture and surface characteristics are important characteristics for successful tissue repair. Both elements can be controlled by the fabrication technique disclosed herein.

Electrospun 3D scaffolds described herein are intended to mimic the structure of natural tendons and thereby provide an environment for seeded tenocytes to secrete ECM and restore tendon tissue function.

The present inventors have found that the use of PCL to make the fibres of the scaffolds of the present invention provides the advantage of a degradation rate that is more appropriate to the growth rate of natural tendons. Furthermore, in vitro degradation studies discussed above show that the degradation products of the scaffold are the expected oligomers and lactones characteristic of PCL degradation.

Embodiments of tissue repair scaffolds as described herein have one or more of the following advantages:

(1) the surface of the scaffold promotes adhesion and/or proliferation of cells and also prevents cell dedifferentiation;

(2) the material used in scaffold manufacture is biodegradable and/or bioresorbable, which eliminates the need for further invasive surgery as the scaffold degrades with time and suitably breakdown products are naturally metabolised;

(3) the scaffold is easily fabricated into the desired shape and size to meet individual patient requirements; and (4) the scaffold is able to temporarily perform the original tissues physical function by demonstrating similar mechanical properties.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Cao Y L, Liu Y T, Liu W, Shan Q X, Buonocore S D, Cui L, (2002), 'Bridging tendon defects using autologous tenocyte engineered tendon in a hen model', *Plastic and Reconstructive Surgery*, 110(5), 1280-1289.

Casper C L, Stephens J S, Tassi N G, Chase D B, Rabolt J F (2004), "Controlling surface morphology of electrospun polystyrene fibres: effect of humidity and molecular weight in the electrospinning process", *Macromolecules*, 37, 573-578.

Crescenze V., Manzini G., Calzolari G., Borri C., "Thermodynamics of fusion of poly b-propiolactone and poly e-caprolactone. Comparative analysis of the melting of aliphatic polylactone and polyester chains". Eur Polym J 1972; 8:449-63.

Curtis A, Wilkinson C, Crossan J, Broadley C, Darmani H, K. K. J, H. J, et al, (2005), 'An in vivo microfabricated scaffold for tendon repair', *Eur Cell Mater*, 9:50-57.

Dzenis Y (2004), "Spinning continuous fibres for nanotechnology", *Science*, 304, 1917-1919.

Fong H, Chun I, Reneker D (1999), "Beaded nanofibres formed during electrospinning", *Polymer*, 40, 4585-4592.

Huang Z M, Zhang Y Z, Kotaki M, Ramakrishna S (2003), "A review on polymer nanofibers by electrospinning and their applications in nanocomposites", *Composites Science and Technology*, 63, 2223-2253.

Maganaris C N, Paul J P, (1999), "In vivo human tendon mechanical properties", *Journal of Physiology*, 521.1, 307-313.

Magnusson S P, Hansen P, Aagaard P, Brond J, Dyhre-Poulsen P, Bojsen-Moller J, Kjaer M, (2003), "Differential strain patterns of the human gastrocnemius aponeurosis and free tendon, in vivo", *Acta Physiologica Scandinavica*, 177 (2), 185-195.

Mit-uppatham C, Nithitanakul M, Supaphol P (2004), "Ultrafine electrospun polyamide-6 fibres: effect of solution conditions on morphology and average fibre diameter", *Macromolecular Chemistry and Physics,* 205, 2327-2338.

Ramakrishna S, Fujihara K, Teo W-E, Lim T-C, Ma Z (2005), "An Introduction to Electrospinning and Nanofibers", World Scientific Publishing Co. Ltd.

Reneker D H, Yarin A L, Fong H, Koombhongse S (2000), "Bending instability of electrically charged liquid jets of polymer solutions in electrospinning", *Journal of Applied Physics,* 87 (9), 4531-4547.

Shawon J, Sung C (2004), "Electrospinning of polycarbonate nanofibres with solvent mixtures THF and DMF", *Journal of Materials Science,* 39, 4605-4613.

Smit E, Buttner U, Sanderson R D (2005), "Continuous yarns from electrospun fibres", *Polymer,* 46, 2419-2423

Smith D J (Jr), Jones C S, Hull M, Kleinert H E, (1986), 'Evaluation of glutaraldehyde-treated tendon xenograft', *J Hand Surg [Am]*, 11(1), 97-106.

Venugopal J, Ma L L, Yong T, Ramakrishna S (2005), "In vitro study of smooth muscle cells on polycaprolactone and collagen nanofibrous matrices", Cell Biology International, 29, 861-867

Wannatong L, Sirivat A, Supahol P (2004), "Effects of solvents on electrospun polymeric fibres:preliminary study on polystyrene", *Polymer International,* 53, 1851-1859.

What is claimed is:

1. A tissue repair scaffold comprising a secondary fibre structure, the secondary fibre structure comprising one or more primary fibre bundles, each primary fibre bundle comprising a plurality of fibres, the fibres comprising polycaprolactone, wherein the average diameter of the fibres is less than 1 μm, wherein the plurality of fibres in each primary fibre bundle are aligned and twisted such that the fibres in each primary bundle form a helix structure.

2. A tissue repair scaffold according to claim 1, wherein the scaffold consists essentially of polycaprolactone.

3. A tissue repair scaffold according to claim 1, wherein the one or more primary fibre bundles are further plaited or twisted to form the secondary fibre structure.

4. A tissue repair scaffold according to claim 1, wherein the secondary fibre structure is a secondary fibre bundle that has a rope-like morphology.

5. A tissue repair scaffold according to claim 1, wherein the average diameter of the primary fibre bundles is in the range 30-100 μm.

6. A tissue repair scaffold according to claim 4, wherein the diameter of the secondary fibre bundle is in the range 150-400 μm.

7. A tissue repair scaffold according to claim 1, wherein the fibres are made by electrospinning.

8. A tissue repair scaffold according to claim 1, wherein the primary fibre bundle comprises at least 50 fibres.

9. A tissue repair scaffold according to claim 1, for use in a method of treatment of the human or animal body, wherein the method comprises treating a damaged tendon.

10. The tissue repair scaffold of claim 1 wherein the secondary fibre structure is a knitted structure knitted from the one or more primary fibre bundles.

11. The tissue repair scaffold of claim 1 wherein the secondary fibre structure is a woven structure woven from the one or more primary fibre bundles.

12. The tissue repair scaffold according to claim 4, wherein the secondary bundle comprises at least 3 primary fibre bundles.

13. The tissue repair scaffold of claim 1 wherein the helix structure has a helix angle in the range of 20°-80°.

14. A tissue repair scaffold comprising a plurality of secondary fibre bundles, each secondary fibre bundle comprising a plurality of primary fibre bundles, wherein each primary fibre bundle comprises a plurality of polycaprolactone fibres that are aligned, each polycaprolactone fibre having an average diameter of less than 1 μm, wherein the plurality of polycaprolactone fibres in each primary fibre bundle are twisted such that the polycaprolactone fibres in each primary fibre bundle form a helix structure.

15. A tissue repair scaffold according to claim 14, wherein each secondary bundle comprises at least 3 primary fibre bundles.

* * * * *